(12) United States Patent
Nowroozi et al.

(10) Patent No.: US 9,498,565 B2
(45) Date of Patent: Nov. 22, 2016

(54) BREAST FLUID EXPRESSION DEVICE

(71) Applicant: Mimeo Labs, Inc., San Francisco, CA (US)

(72) Inventors: Bryan Neema Nowroozi, San Francisco, CA (US); Edward Jaebum Park, San Francisco, CA (US)

(73) Assignee: Mimeo Labs, Inc., San Francisco, CA (US)

( * ) Notice: Subject to any disclaimer, the term of this patent is extended or adjusted under 35 U.S.C. 154(b) by 0 days.

(21) Appl. No.: 14/835,472

(22) Filed: Aug. 25, 2015

(65) Prior Publication Data

US 2016/0058928 A1  Mar. 3, 2016

Related U.S. Application Data

(60) Provisional application No. 62/042,200, filed on Aug. 26, 2014, provisional application No. 62/052,792, filed on Sep. 19, 2014, provisional application No. 62/091,403, filed on Dec. 12, 2014.

(51) Int. Cl.
*A61M 1/06* (2006.01)

(52) U.S. Cl.
CPC .............. *A61M 1/064* (2014.02); *A61M 1/06* (2013.01); *A61M 1/062* (2014.02); *A61M 1/066* (2014.02);
(Continued)

(58) Field of Classification Search
CPC ...... A61M 1/064; A61M 1/062; A61M 1/06; A61M 1/066; A61M 2205/502; A61M 2205/0216; A61M 2205/33; A61M 2205/3584
USPC .................................................... 604/74, 75
See application file for complete search history.

(56) References Cited

U.S. PATENT DOCUMENTS 2,396,544 A    3/1946  Voyle et al.
4,263,912 A    4/1981  Adams
(Continued)

FOREIGN PATENT DOCUMENTS

CA    1313804    2/1993
EP    0198469    10/1986
(Continued)

OTHER PUBLICATIONS

Badeer, Henry S. "Hemodynamics for medical students." Advances in physiology education 25.1 (2001): 44-52.
(Continued)

*Primary Examiner* — Laura Bouchelle
*Assistant Examiner* — Anh Bui
(74) *Attorney, Agent, or Firm* — Knobbe, Martens, Olson & Bear, LLP

(57) ABSTRACT

Disclosed herein are biologically inspired, either manual or electronic, portable fluid expression system to be used for, but not limited to, breast milk expression from nursing women and other milk expression from any species of mammal. The fluid expression systems can be configured to mimic the anatomy of a suckling infant and the biomechanics and fluid dynamics associated with this behavior. The fluid expression system can be used by nursing mothers to express breast milk efficiently, painlessly, and discreetly. The systems can include a single, contiguous flexible structure designed to resemble the lips and oropharyngeal cavity of a newborn infant of the mammalian species of interest. Rigid external housings or stiffening structures can be used to mimic the bony anatomy of the infant or mammalian species of interest.

20 Claims, 28 Drawing Sheets

(52) U.S. Cl.
CPC .. *A61M 2205/0216* (2013.01); *A61M 2205/33* (2013.01); *A61M 2205/3584* (2013.01); *A61M 2205/50* (2013.01); *A61M 2205/502* (2013.01); *A61M 2205/52* (2013.01)

(56) References Cited

U.S. PATENT DOCUMENTS

| | | |
|---|---|---|
| 4,323,067 A | 4/1982 | Adams |
| 4,772,262 A | 9/1988 | Grant et al. |
| 4,929,229 A | 5/1990 | Larsson |
| 4,964,851 A | 10/1990 | Larsson |
| 5,218,924 A | 6/1993 | Thompson et al. |
| 5,571,084 A | 11/1996 | Palmer |
| 6,004,288 A | 12/1999 | Hochstedler et al. |
| 6,579,258 B1 | 6/2003 | Atkin et al. |
| 6,663,587 B2 † | 12/2003 | Silver |
| 6,808,517 B2 | 10/2004 | Greter et al. |
| 7,223,255 B2 | 5/2007 | Myers et al. |
| 7,396,340 B2 | 7/2008 | Onuki et al. |
| 7,479,125 B2 | 1/2009 | Tashiro |
| 7,662,127 B2 | 2/2010 | Silver et al. |
| 7,824,363 B2 | 11/2010 | Myers |
| 7,972,297 B2 | 7/2011 | Bryan et al. |
| 7,988,661 B2 | 8/2011 | Silver et al. |
| 8,052,634 B2 | 11/2011 | Thommen et al. |
| 8,052,635 B1 | 11/2011 | Kelly et al. |
| 8,070,715 B2 | 12/2011 | Quackenbush et al. |
| 8,070,716 B2 | 12/2011 | Quackenbush et al. |
| 8,118,772 B2 | 2/2012 | Dao et al. |
| 8,137,305 B2 | 3/2012 | Kelly et al. |
| 8,142,393 B2 | 3/2012 | Myers et al. |
| 8,152,754 B2 | 4/2012 | Silver et al. |
| 8,323,235 B2 † | 12/2012 | Bryan |
| 8,398,584 B2 | 3/2013 | Britto |
| 8,465,449 B2 | 6/2013 | Guo |
| 8,465,450 B2 | 6/2013 | Guo |
| 8,469,770 B2 | 6/2013 | Alva |
| 8,480,451 B2 | 7/2013 | Solberg |
| D688,785 S | 8/2013 | Cudworth |
| D688,786 S | 8/2013 | Cudworth |
| 8,512,010 B2 | 8/2013 | Stutz et al. |
| 8,523,804 B2 | 9/2013 | Cudworth |
| 8,529,501 B2 | 9/2013 | Wach et al. |
| 8,545,438 B2 | 10/2013 | Kazazoglu et al. |
| 8,551,040 B2 | 10/2013 | Tack et al. |
| 8,568,350 B2 | 10/2013 | Schlienger et al. |
| 8,579,874 B1 | 11/2013 | Barack |
| 8,801,658 B2 | 8/2014 | Harari et al. |
| 8,827,947 B2 | 9/2014 | Bosman |
| 2002/0198489 A1* | 12/2002 | Silver ............... A61M 1/06 604/74 |
| 2003/0073951 A1 | 4/2003 | Morton et al. |
| 2005/0154349 A1 | 7/2005 | Renz et al. |
| 2005/0234370 A1 | 10/2005 | Beal et al. |
| 2010/0094078 A1 | 4/2010 | Weston |
| 2010/0121263 A1 | 5/2010 | Farka et al. |
| 2010/0121264 A1* | 5/2010 | Bryan ............... A61M 1/06 604/74 |
| 2010/0130921 A1* | 5/2010 | Kobayashi ......... A61M 1/06 604/74 |
| 2010/0217148 A1 | 8/2010 | Binder |
| 2011/0071466 A1 | 3/2011 | Silver et al. |
| 2011/0118627 A1 | 5/2011 | Morton et al. |
| 2011/0239943 A1 | 10/2011 | Hanskamp |
| 2011/0251552 A1 | 10/2011 | Brittner |
| 2012/0004604 A1 | 1/2012 | Van Der Kamp et al. |
| 2012/0029424 A1 | 2/2012 | Greter et al. |
| 2012/0116298 A1 | 5/2012 | Van Schijndel et al. |
| 2012/0289934 A1 | 11/2012 | Greter et al. |
| 2013/0023821 A1 | 1/2013 | Khalil et al. |
| 2014/0031744 A1 | 1/2014 | Chen |
| 2014/0121593 A1 | 5/2014 | Felber et al. |
| 2014/0263611 A1 | 9/2014 | Bauer |
| 2014/0288466 A1* | 9/2014 | Alvarez ............. A61M 1/06 601/6 |
| 2014/0378895 A1* | 12/2014 | Barack .............. A61M 1/064 604/74 |

FOREIGN PATENT DOCUMENTS

| | | |
|---|---|---|
| EP | 2502639 | 9/2012 |
| WO | WO 2016/014494 | 1/2016 |

OTHER PUBLICATIONS

Bu'Lock, Frances, M. W. Woolridge, and J. D. Baum. "Development of co-ordination of sucking, swallowing and breathing: Ultrasound study of term and preterm infants." Developmental Medicine & Child Neurology 32.8 (1990): 669-678.

Colley, J. R. T., and B. Creamer. "Sucking and swallowing in infants." British medical journal 2.5093 (1958): 422-423.

Cornall, Denise. "A review of the breastfeeding literature relevant to osteopathic practice." International Journal of Osteopathic Medicine 14.2 (2011): 61-66.

da Costa, Saakje P., et al. "Sucking patterns in fullterm infants between birth and 10 weeks of age." Infant Behavior and Development 33.1 (2010): 61-67.

Diewert, Virginia M. "A morphometric analysis of craniofacial growth and changes in spatial relations during secondary palatal development in human embryos and fetuses." American journal of anatomy 167.4 (1983): 495-522.

Eishima, Kazuko. "The analysis of sucking behaviour in newborn infants." Early human development 27.3 (1991): 163-173.

Elad, David, et al. "Biomechanics of milk extraction during breast-feeding." Proceedings of the National Academy of Sciences 111.14 (2014): 5230-5235.

Fewtrell, Mary S., et al. "Randomized trial comparing the efficacy of a novel manual breast pump with a standard electric breast pump in mothers who delivered preterm infants." Pediatrics 107.6 (2001): 1291-1297.

Geddes, Donna T. "Inside the lactating breast: the latest anatomy research." Journal of Midwifery & Women's Health 52.6 (2007): 556-563.

Geddes, Donna T. "Ultrasound imaging of the lactating breast: methodology and application." International Breastfeeding Journal 4.1 (2009): 1 in 17 pages.

Geddes, Donna T., et al. "Tongue movement and intra-oral vacuum in breastfeeding infants." Early human development 84.7 (2008): 471-477.

Geddes, Donna T., et al. "Tongue movement and intra-oral vacuum of term infants during breastfeeding and feeding from an experimental teat that released milk under vacuum only." Early human development 88.6 (2012): 443-449.

Geddes, Donna T., et al. "Ultrasound imaging of infant swallowing during breast-feeding." Dysphagia 25.3 (2010): 183-191.

Gerling, Gregory J., and Geb W. Thomas. "Augmented, pulsating tactile feedback facilitates simulator training of clinical breast examinations." Human Factors: The Journal of the Human Factors and Ergonomics Society 47.3 (2005): 670-681.

Gooding, Mark J., et al. "Three-Dimensional Ultrasound Imaging of mammary ducts in lactating women a feasibility study." Journal of Ultrasound in Medicine 29.1 (2010): 95-103.

Green, Dolly, et al. "The relative efficacy of four methods of human milk expression." Early human development 6.2 (1982): 153-159.

Han, Lianghao, et al. "Development of patient-specific biomechanical models for predicting large breast deformation." Physics in Medicine and Biology 57.2 (2011): 455-472.

Hassiotou, Foteini, and Donna Geddes. "Anatomy of the human mammary gland: Current status of knowledge." Clinical anatomy 26.1 (2013): 29-48.

Hayashi, Yoshihiro, Eiichi Hoashi, and Takahiro Nara. "Ultrasonographic analysis of sucking behavior of newborn infants: the driving force of sucking pressure." Early human development 49.1 (1997): 33-38.

(56) References Cited

OTHER PUBLICATIONS

Hopkinson, Judy, and William Heird. "Maternal response to two electric breast pumps." Breastfeeding Medicine 4.1 (2009): 17-23.
Hutchinson, Erin F., Jules A. Kieser, and Beverley Kramer. "Morphometric growth relationships of the immature human mandible and tongue." European journal of oral sciences 122.3 (2014): 181-189.
Jacobs, Lorili Audrey, et al. "Normal nipple position in term infants measured on breastfeeding ultrasound." Journal of Human Lactation 23.1 (2007): 52-59.
Kent, Jacqueline C., et al. "Effect of warm breastshields on breast milk pumping." Journal of Human Lactation 27.4 (2011): 331-338.
Kent, Jacqueline C., et al. "Importance of vacuum for breastmilk expression." Breastfeeding Medicine 3.1 (2008): 11-19.
Lundqvist, Christian, and Maria Hafström. "Non-nutritive sucking in full-term and preterm infants studied at term conceptional age." Acta Paediatrica 88.11 (1999): 1287-1289.
McClellan, Holly L., et al. "Validation of nipple diameter and tongue movement measurements with B-mode ultrasound during breastfeeding." Ultrasound in medicine & biology 36.11 (2010): 1797-1807.
Miller, Jeri L., and Seon M. Kang. "Preliminary ultrasound observation of lingual movement patterns during nutritive versus non-nutritive sucking in a premature infant." Dysphagia 22.2 (2007): 150-160.
Mizuno, Katsumi, and Aki Ueda. "Changes in sucking performance from nonnutritive sucking to nutritive sucking during breast- and bottle-feeding." Pediatric research 59.5 (2006): 728-731.
Monaci, Gianluca, and Mike Woolridge. "Ultrasound video analysis for understanding infant breastfeeding." Image Processing (ICIP), 2011 18th IEEE International Conference on. IEEE, 2011 in 4 pages.
Prime, Danielle K., et al. "Comparison of the patterns of milk ejection during repeated breast expressin sessions in women." Breastfeeding Medicine 6.4 (2011): 183-190.
Ramsay, Donna T., et al. "Milk flow rates can be used to identify and investigate milk ejection in women expressing breast milk using an electric breast pump." Breastfeeding Medicine 1.1 (2006): 14-23.
Ramsay, Donna T., et al. "The use of ultrasound to characterize milk ejection in women using an electric breast pump." Journal of Human Lactation 21.4 (2005): 421-428.
Ramsay, Donna T., et al. "Ultrasound imaging of milk ejection in the breast of lactating women." Pediatrics 113.2 (2004): 361-367.
Roberts, Kathryn L., Maureen Reiter, and Diane Schuster. "Effects of cabbage leaf extract on breast engorgement." Journal of Human Lactation 14.3 (1998): 231-236.
Rusby, Jennifer E., et al. "Breast duct anatomy in the human nipple: three-dimensional patterns and clinical implications." Breast cancer research and treatment 106.2 (2007): 171-179.
Sakalidis, Vanessa S., et al. "Ultrasound imaging of infant sucking dynamics during the establishment of lactation." Journal of Human Lactation 29.2 (2013): 205-213.
Samani, Abbas, and Donald Plewes. "A method to measure the hyperelastic parameters of ex vivo breast tissue samples." Physics in Medicine and Biology 49.18 (2004): 4395-4405.
Samani, Abbas, and Donald Plewes. "An inverse problem solution for measuring the elastic modulus of intact ex vivo breast tissue tumours." Physics in medicine and biology 52.5 (2007): 1247.
Sasamoto, Yuki, Naoto Nishijima, and Asada Minoru. "Towards understanding the origin of infant directed speech: A vocal robot with infant-like articulation." Development and Learning and Epigenetic Robotics (ICDL), 2013 IEEE Third Joint International Conference on. IEEE, 2013 in 2 pages.
Schaal, Benoist, et al. "Human breast areolae as scent organs: Morphological data and possible involvement in maternal-neonatal coadaptation." Developmental psychobiology 48.2 (2006): 100-110.
Siebert, J. R. "A morphometric study of normal and abnormal fetal to childhood tongue size." Archives of oral biology 30.5 (1985): 433-440.
Smith, Wilbur L., Allen Erenberg, and Arthur Nowak. "Imaging evaluation of the human nipple during breast-feeding." American Journal of Diseases of Children 142.1 (1988): 76-78.
Tamura, Yasuo, Yoko Horikawa, and Sadahiro Yoshida. "Co-Ordination of Tongue Movements and Peri-Oral Muscle Activities During Nutritive Sucking." Developmental Medicine & Child Neurology 38.6 (1996): 503-510.
Vorperian, Houri K., et al. "Anatomic development of the oral and pharyngeal portions of the vocal tract: An imaging studya)." The Journal of the Acoustical Society of America 125.3 (2009): 1666-1678.
Vorperian, Houri K., et al. "Development of vocal tract length during early childhood: A magnetic resonance imaging study." The Journal of the Acoustical Society of America 117.1 (2005): 338-350.
Vorperian, Houri K., et al. "Magnetic resonance imaging procedures to study the concurrent anatomic development of vocal tract structures: preliminary results." International Journal of Pediatric Otorhinolaryngology 49.3 (1999): 197-206.
Woolridge, M. W., et al. "The continuous measurement of milk intake at a feed in breast-fed babies." Early human development 6.4 (1982): 365-373.
Woolridge, Michael W. "The 'anatomy' of infant sucking." Midwifery 2.4 (1986): 164-171.
Zinaman, Michael J., et al. "Acute prolactin and oxytocin responses and milk yield to infant suckling and artificial methods of expression in lactating women." Pediatrics 89.3 (1992): 437-440.
International Search Report and Written Opinion in PCT Application No. PCT/US2015/046789 dated Dec. 10, 2015 in 9 pages.

\* cited by examiner
† cited by third party

BREAST FLUID EXPRESSION DEVICE

REFERENCE TO RELATED APPLICATIONS

This application claims the benefit under 35 U.S.C. §119 (e) as a nonprovisional application of each of U.S. Prov. Pat. App. Nos. 62/042,200 filed on Aug. 26, 2014; 62/052,792 filed on Sep. 19, 2014; and 62/091,403 filed on Dec. 12, 2014. Each of the foregoing priority applications is hereby incorporated by reference in their entireties.

BACKGROUND

The majority of biological fluid expression devices on the market today typically include some combination of the following parts: a breastshield assembly, collection bottles and/or bags, vacuum tubing, a high volume vacuum pump head, a direct drive motor, a battery pack, a power supply jack, and a controller.

Breastshield assemblies typically comprise a funnel shaped rigid outer shell, sometimes called a breastcup, and a tubular conduit structure sometimes referred to as a nipple tube. The funnel shaped breastcup has an area formed to receive a breast and nipple. While the majority of current pumps on the market today have rigid breastcups, the inclusion of a soft liner is sometimes allowed in an attempt to aid in sizing, comfort and fluid expression.

The nipple tube is typically made of plastic and/or silicone, but in some cases other materials are allowed for, to connect the breastcup to the container receptacle. The nipple tunnel is typically shaped to receive the nipple without collapsing, and often results in substantial movement and stretching of the nipple during expression. This tunnel is often used to allow an entry point for applying vacuum to express fluids.

On the opposite end of the nipple tube typically lies a receptacle of some sort. Often times the nipple tube terminates in a threaded fitting to allow the attachment of a plastic or glass bottle. In addition, polyethylene fluid storage bags, or bags of a variety of materials, have been used here to allow pumping into bags for freezer storage.

The entire assembly is pressurized with a negative pressure vacuum, forming a seal between the breast and the breastshield. When turned on, the vacuum begins to generate a cyclic pressure gradient using a diaphragm, piston, or bellows structure that typically vents to atmospheric pressure on the completion of each stroke cycle. In some instances, the diaphragm, bellows, or piston structure is manipulated using a linear actuation mechanism. This mechanism can be a rotary electric motor, a servomotor, or some other electromechanical system that moves an actuator arm through a reciprocating linear motion for the instroke and outstroke to generate the pressure waveform. This allows alternating positive and negative pressure to be introduced into the nipple tunnel for each stroke cycle. The duty cycle of each stroke is typically intended to mimic the suck-release profile of the suckling infant, with operating profiles with duty cycles in the one-half to two-thirds range targeted. Pumps typically target a frequency of 45-60 Hz again in an attempt to mimic a live suckling infant.

The negative pressure is transmitted from the vacuum to the nipple tunnel via the vacuum tubing, creating a pressurized chamber comprised of the breastcup, nipple tunnel, and the receptacle. In some devices gravity causes fluid to flow from the breast cup into the collection bottle, while other devices include valves to separate the receptacle during negative pressure generation to allow milk expression from the nipple into the nipple tunnel. Subsequently, the valve is opened and the system is vented to atmospheric pressure to allow fluid movement from the nipple tunnel into the receptacle.

Most of the commercially available pumps on the market today have characteristics that make them operate less efficiently than a nursing baby and with a higher degree of discomfort. The rigidity of the breastcup structures affects efficiency in that the funnel and nipple tube are not collapsible and therefore operate at large dead air volumes, depending on where the vacuum is plumbed into the assembly and where the valves are positioned, the amount of dead air volume that the pump must affect can vary. When dead air volume is not minimized, additional pressure is required to express liquid from the breast. This design is present in the majority of breast pumps on the market, and results in systems that generate maximum negative pressures between −200 and −500 mm Hg.

This increase in vacuum pressure also results in greater discomfort for the user. The nipple and surrounding tissue is pulled and stretched more dramatically within the nipple tunnel. Research has shown that movement of the nipple within the infant's mouth is on the order of 2 mm. This much greater movement seen in current nipple tube design increases discomfort and might constrict the terminal ends of the lactiferous ducts, thereby impeding fluid flow. Moreover, the excess breast tissue engaged by the large, rigid funnel of the breastcup applies the greater pressure to more sensitive anatomy.

Similarly, the current devices do not offer any method of quantifying certain environmental and biomechanical data regarding pumping biomechanics and efficiency to assist nursing mothers, or lactation consultants, in better evaluating and programming expression devices. Variables of interest could include, but are not limited to, fluid volume per minute, temperature of fluid, number of let-downs, pressure within devices, cycle parameters, duty cycle times, protein content, fat content, and overall time of usage. Knowledge of these variables is absent in current designs, and if included, could allow users to implement more efficient cycling programs, timing schedules to generate more efficient fluid expression and have a better understanding of the overall milk production and quality expressed via the device. In addition, automated feedback algorithms could be incorporated to use this data to automatically adjust cycle parameters during a session to increase efficiency. For example, current pumps on the market transition between nutritive and non-nutritive sucking cycle based entirely on previously programmed timers, or on user input. However, this assumes that all infants transition from non-nutritive to nutritive at the same time, and only once per sucking cycle, which we know to be inaccurate. Therefore, an automated transition between non-nutritive and nutritive suckling waveforms based on quantification of pressure and fluid flow within the system would allow multiple transitions during an expression session that would not require user input, and would improve expression efficiency. Further, many pumps include a controller system having a keypad or dial for user input. The controller offers the user the ability to program the lactation cycles by choosing various settings typically focusing on vacuum magnitude and cycle frequency. However, there is currently no pump available to consumers that is capable of sensing various internal fluid expression variables and modulating device settings automatically to optimize expression.

Finally, current pumps do not allow for mobile/smartphone control of devices, wireless connectivity between tablet and/or smartphones and devices, wireless cloud syncing and online device analysis, or comparative analysis and social networking with regards to device usage for users. The ability to wirelessly, and automatically upload environmental data to an online portal for personal analysis, as well as comparative analysis with the device community, is one that would assist many nursing mothers in improving pumping efficiency. This capability has not, to the inventors' knowledge, been included in any previous device.

The multitude of differences between the anatomy and biomechanics of a suckling infant and the structure and mechanics of current pumping devices result in lower efficiency, increased discomfort, decreased discretion, and bulky design. These problems combined with the lack of automation and updated connectivity to web/mobile devices leave room for innovation and increases in efficiency. Embodiments of the present invention aim in some aspects to solve these problems by implementing a biomimetic design of a fluid expression device to be used in both humans, as well as other mammals, combined with the inclusion of environmental sensors and web/mobile connectivity to control, automate, and analyze device and user function and biomechanics.

SUMMARY

The aforementioned disadvantages of traditional breast pumps can be overcome by implementing biomimetic design principles towards a fluid expression device that accurately mimics the interface between mother and infant of any mammalian species, including humans. The design can, in some embodiments, mimic the anatomy of the oropharynx of a suckling infant for each species in a single, flexible contiguous structure used within a device that will generate the pressure differentials required for fluid expression via mechanics similar to those observed in an infant, instead of relying solely on high volume vacuum pumps. In this way, appropriate pressure load can be applied to both the lactiferous ducts of the nursing mother and the artificial oropharynx designed for the device, thereby properly optimizing the device for the fluid dynamics regimes of both the nursing mother and the device itself. In addition, in using materials that mimic the soft tissues of an infant's lips and oropharynx, the device can take advantage of the passive soft tissue mechanics associated with manipulation of the pressure vessel to improve performance without increasing energy costs. Further, the biomimetic design of the soft, flexible structure should stimulate physiological responses in nursing mothers including increased prolactin and oxytocin concentrations to levels seen during breastfeeding. These changes in structure and mechanics should improve efficiency to rival that of a suckling infant. In addition to these novel changes in structure and mechanics, some embodiments include environmental sensors to monitor variables of interest including, but not limited to, pressure within the device, fluid flow within the device, volume expressed, temperature of fluid, duty cycle of the device, total time of expression, and fluid expression schedule throughout each 24 hour period. This data can be used to automate changes in suckling pressure and cycle waveform to optimize efficiency for each user. In addition, the data will allow multiple transitions between nutritive and non-nutritive sucking during an expression session based on environmental variable quantification within the device. This data can then be collected via smartphone and web connectivity to allow analysis of personal data, as well as comparative analysis with the community of users of the device.

The smartphone connectivity will also allow programming and control of the device in addition to an on-device control panel. Finally, the change in mechanics, design, and improvement in electronics can allow for lower, more efficient battery requirements, and can ultimately result in a quieter and lower-profile device that will increase the ease of portability.

In some embodiments, disclosed herein is a mammalian fluid expression device. The device can include a soft, contiguous, collapsible structure having an internal channel therethrough that can receive a nipple-areola complex and connect to a receptacle. When actuated via a fluid expression system, the soft structure is configured to be repeatedly asymmetrically deformed to express fluid. Upon fluid expression, fluid is transported into the receptacle. The device can also include a manually engaged piston calibrated to set the baseline pressure. The device can also include a rotary shaft or lever arm to allow manual actuation of the inferior aspect of the structure resulting in negative pressure gradients within the internal volume for fluid expression. The device can also include at least one environmental sensor within the structure, within the housing, and/or within the receptacle to allow the capturing of environmental data. The device can also include a controller configured to process and quantify the data and make the data available for user and researcher data collection and analysis, as well as used to automate pump settings specific to individual users, and optimize fluid expression and minimize discomfort. The pumping cycle of the device can, in some cases, automatically transition between a stimulative and non-stimulative cycle multiple times throughout a pumping session. The device can also be configured to be controlled using a web/mobile user interface accessible from a user's smartphone, tablet, laptop, desktop, or another remotely-connectable device.

In some embodiments, also disclosed herein is a single, contiguous, partially collapsible structure that includes a biocompatible, flexible material configured to receive a nipple-areola complex. The structure can include a proximal end with a circular, elliptical, or other geometric cross-sectional or end profile configured to receive a nipple-areola complex. The structure can also include an external rigid housing configured to mimic an infant's oropharyngeal cavity. The housing can include, in some cases, stiffening elements. The stiffening elements can be in some cases configured to replicate the bony anatomy and the form of the inferior aspect of the oropharyngeal cavity during peak negative pressure while breastfeeding. The housing can be configured to receive the single, continuous structure within the housing. The distal end of the structure can have a smaller diameter than the proximal end and be configured to connect to a receptacle or vacuum. A continuous vacuum can be used to generate constant baseline sub-atmospheric pressure, resulting in a primed system state. Asymmetric volume deformation via elevation and depression of the length of an inferior aspect of the structure away from a superior, stiffer, aspect of the structure can create an interior volume modulation of the single contiguous structure resulting in negative pressure gradients within the internal volume for fluid expression. In some embodiments, the oropharyngeal portion has variable thicknesses circumferentially such that the thickness of the material increases gradually from the inferior aspect up along the lateral aspect and towards the superior aspect of the structure. The superior portion can mimic the hard and soft palates of the infant. In some embodiments, the anterior portion is the thickest, most stiff portion of the structure, and the posterior portion is thinner and/or less stiff than the anterior portion. In some embodiments, upon generation of constant baseline sub-atmospheric pressure, the variation in stiffness of the structure allows for asymmetrical collapse along the length of the inferior aspect of the structure against the superior, stiffer, portion of the structure while accommodating the received nipple-areola complex. The device can also include a manually engaged piston calibrated to set the baseline pressure, and/or a rotary shaft or lever arm to allow manual actuation of the inferior aspect of the structure resulting in negative pressure gradients within the internal volume for fluid expression. The device can also be configured such that once fluid has been expressed into the device, the fluid is transported to a receptacle by gravity, the receptacle operably connectable to a distal end of the device. The device can also be configured such that once fluid has been expressed into the device, the vacuum pressure of a continuous vacuum head operably connected to the structure is increased such that the peak magnitude of the baseline vacuum drops below the initial baseline, such that as the actuation is returned to an initial starting position, the fluid is drawn into the receptacle by the lower pressure, and upon the end of the stroke the baseline vacuum returns to the original baseline. In some embodiments, the device can be configured such that the initial starting position of an inferior aspect of the soft structure is incrementally lower than a final resting position, such that the pressure generated upon attaining the final resting position of each stroke cycle is greater than the initial pressure at the starting position, such that the fluid is drawn into the receptacle below by the lower pressure. The device can include one, two, or more sensors within the structure, within the housing, and/or within the receptacle to allow the capturing of environmental data. The device can also include a controller configured to process and quantify the data and make the data available for user and researcher data collection and analysis, as well as used to automate pump settings specific to individual users, and optimize fluid expression and minimize discomfort. In some embodiments, the pumping cycle is configured to automatically transition between a stimulative and non-stimulative cycle multiple times throughout a pumping session. The device can be configured to be controlled using a web/mobile user interface accessible from a user's smartphone, tablet or another remotely connectable device.

In some embodiments, a mammalian fluid expression device can include a single, contiguous, partially collapsible structure having a proximal end and a distal end and comprising a biocompatible, flexible material configured to receive a nipple-areola complex, The structure can include a proximal end with an elliptical profile configured to receive a nipple-areola complex. The structure can also include an inferior aspect and a superior aspect, wherein the superior aspect has a stiffness that is greater than that of the inferior aspect. The device can also include a housing which can be rigid in some cases. The housing can be configured to house the soft, contiguous structure therein to, in some cases, mimic an infant's oropharyngeal cavity. The distal end of the structure can have a smaller diameter than the proximal end, and be configured to connect to a receptacle or vacuum. The device can be configured such that asymmetric volume deformation via elevation and depression of the length of the inferior aspect of the structure away from the superior, stiffer, aspect of the structure creates an interior volume modulation of the single contiguous structure resulting in negative pressure gradients within the internal volume for fluid expression.

In some embodiments, disclosed herein is a mammalian fluid expression device that includes a single, hollow, contiguous, collapsible structure made of a biocompatible, flexible material configured to receive a nipple-areola complex. The structure can include a proximal end with an elliptical profile capable of receiving a nipple-areola complex. The distal end of the structure can include a smaller diameter than the proximal end, and be configured to connect to a receptacle or vacuum. The device can be configured such that when continuous vacuum is used to generate constant baseline sub-atmospheric pressure, the interior volume around the received nipple-areola complex is configured to collapse resulting in a primed system state. In some embodiments, asymmetric volume deformation via elevation and depression of the inferior aspect of the structure away from the superior, thicker, aspect of the structure creates an interior volume modulation of the single contiguous structure resulting in negative pressure gradients within the internal volume for fluid expression. In some embodiments, the device can include a superior and inferior hollow shell structure configured to allow the housing of, for example, electronics, batteries, vacuum pump systems, and/or actuation systems. In some embodiments, once fluid has been expressed into the device, the fluid can be transported to a receptacle by gravity. The receptacle can be operably connectable to a distal end of the device. In some embodiments, the device can be configured such that wherein once fluid has been expressed into the device, the vacuum pressure of a continuous vacuum head operably connected to the structure is increased such that the peak magnitude of the baseline vacuum drops below the initial baseline, such that as the actuation is returned to an initial starting position, the fluid is drawn into the receptacle by the lower pressure, and upon the end of the stroke the baseline vacuum returns to the original baseline. In some embodiments, an initial starting position of an inferior aspect of the soft structure is incrementally lower than a final resting position, such that the pressure generated upon attaining the final resting position of each stroke cycle is greater than the initial pressure at the starting position, such that the fluid is drawn into the receptacle below by the lower pressure. The device can also include a peristaltic pump positioned near the distal portion of the soft, contiguous structure to facilitate fluid transport from the internal volume of the soft structure into a receptacle connectable to the distal end of the structure. In some embodiments, a device can include a heating element to encourage prolactin and oxytocin production in the nursing mother.

Also disclosed herein is a mammalian fluid expression device. The device can include a single, patent, contiguous, collapsible structure made of a biocompatible, flexible material configured to receive a nipple-areola complex. The structure can include a proximal end with an elliptical profile capable of receiving a nipple-areola complex, an oropharyngeal portion having variable thicknesses circumferentially such that the thickness of the material increases gradually from the inferior aspect up along the lateral aspect and towards the superior aspect of the structure, a superior portion that mimics the hard and soft palates of the infant, wherein the anterior portion is the thickest, most stiff portion of the structure, and the posterior portion is thinner, and/or a distal end of the structure with a smaller diameter than the proximal end, and capable of connecting to a receptacle or vacuum. In some embodiments, the device can be configured such that a continuous vacuum is used to generate constant baseline sub-atmospheric pressure. The variation in the thickness of the portions can allow for asymmetrical collapse of the inferior aspect of the structure against the superior, thicker, portion of the structure while accommodating the received nipple-areola complex resulting in a primed system state. The device can also be configured such that volume deformation via elevation and depression of the inferior aspect of the structure away from the superior, thicker, aspect of the structure creates an interior volume modulation of the single contiguous structure resulting in negative pressure gradients within the structure for fluid expression.

In some embodiments, a fluid expression device can include a flexible unitary body that can include a proximal opening sized to receive a nipple-areola complex, the proximal opening having a first diameter, a distal opening having a second diameter smaller than the first diameter, and a channel fluidly connecting the proximal opening and the distal opening. The flexible unitary body can further have a sidewall having a variable thickness through a longitudinal section of the sidewall. The sidewall can be configured to asymmetrically collapse upon the application of vacuum within the channel. The flexible unitary body can be at least partially contained within a rigid or semi-rigid housing. In some embodiments, the sidewall can include a superior zone and an inferior zone, and the superior zone is stiffer than the inferior zone. The sidewall can also include a lateral zone that is stiffer than the inferior zone, but not as stiff as the superior zone. The device can also include an actuator operably connected to the inferior zone of the flexible unitary body.

In some embodiments, disclosed herein is a kit for fluid expression. The kit can include a fluid expression device, a fluid reservoir reversibly connectable to the distal opening of a flexible unitary body of the device; and/or a source of vacuum.

Also disclosed herein are methods for expressing fluid from a breast. The methods can include positioning the proximal opening of a fluid expression device proximate a nipple-areola complex. The proximal opening can be positioned such that the opening does not or does not substantially contact breast tissue outside the nipple-areola complex. The fluid expression device can include an elongate body having a central channel fluidly connected to the proximal opening, a distal opening, a superior zone, and an inferior zone. Moving an inferior zone of the elongate body toward the superior zone of the elongate body can asymmetrically collapse the central channel, thereby moving fluid from the nipple-areola complex into the channel and toward the distal opening.

DETAILED DESCRIPTION

Figure 1A:
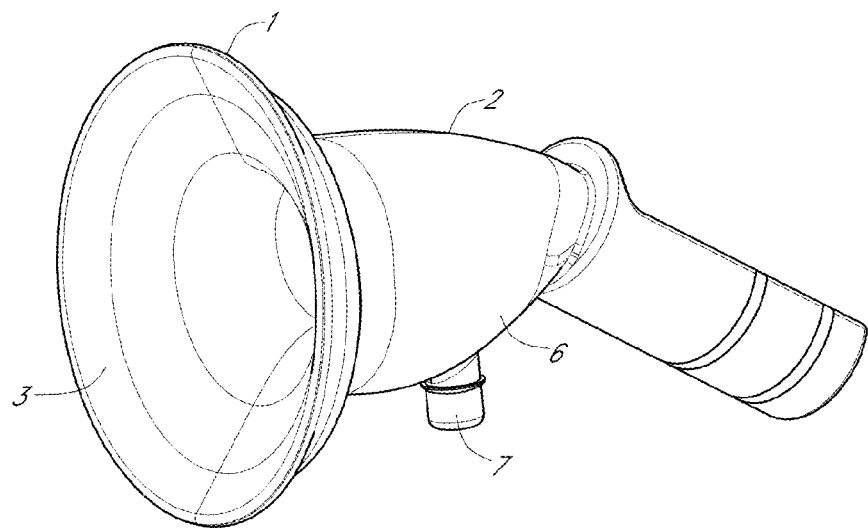
FIG. 1A is an anterior perspective view of a biomimetic designed structure for use with a fluid expression device showing the single contiguous structure housed within a rigid external housing.

Recent studies investigating the mechanics of breastfeeding in infants have revealed that infants generate a constant baseline pressure that remains sub-atmospheric and is modulated with a simple actuation to ensure efficient fluid flow regimes not only in the oropharynx of the infant, but also within the lactiferous ducts of the nursing mother. This is done by minimizing dead air volume to amplify the effects of the tongue's mechanical actuation allowing the infant to achieve optimal negative pressure magnitudes for fluid expression through the biological system.

At the resting position, the nipple is held firmly and fully within the infant's mouth with the tongue positioned beneath the nipple, but not markedly indenting the nipple border, or compressing the nipple. The soft palate is relaxed, and the nasopharynx has a clear path to the trachea. Laterally, the tongue and buccal mucosa form a seal around the nipple, and extend up to the roof of the mouth. The breastfeeding infant then draws a constant baseline vacuum that results in asymmetrical collapse of the internal oral cavity around the nipple and up towards the hard palate. There is effectively no space between the tongue, the buccal surfaces, the hard palate, and the nipple. The nipple is completely encased, but not indented or compressed. The posterior tongue is in close proximity, and in many cases in contact with, the junction between the hard and soft palate. With a proper seal of the infant's lips around the nipple, the baseline pressure within the oropharynx minimizes dead air volume in the system. In humans, this baseline pressure can range, typically with a mean around −45 to −60 mm Hg. In some embodiments the anatomical structure of the system can be important for the generation of a proper latch, as well as in applying the appropriate pressure to the appropriate mammary anatomy. The typical circular funnel shaped flange of existing devices, as well as the rigid cylindrical shape of the nipple tube, are a marked departure from the appropriate anatomical structure and result in increased pressure requirements, as well as substantial stretching of the nipple, that can lead to painful, inefficient fluid expression.

Following latching, the lower jaw elevates until the moment that the medial portion of the tongue is elevated such that the nipple's height has decreased, and a positive sucking pressure, relative to the negative baseline pressure, is generated. At this point a traveling wave of tongue depression proceeds posterior-inferiorly along the length of the tongue, facilitating a downward movement of the posterior portion of the tongue in a somewhat linear fashion. This tongue depression, and depression of the lower jaw in a posterior-inferior direction, generates a negative pressure peaking at a mean of −114 to −145 mm Hg. Thus, the infant generates negative pressure by asymmetrically modulating the volume of the oral cavity at the point of the hard-soft palate junction by depressing and elevating the tongue. This negative pressure draws fluid from the lactiferous ducts into the oropharynx via the inferior depression of the tongue. The peak pressures generated are substantially lower than those generated in current breast pump designs, and likely have an impact on the efficiency of fluid expression based on the fluid dynamics regimes that govern both the lactiferous ducts of the nursing mother and the oropharynx of the suckling infant.

Once fluid has been drawn into the oropharynx, the anterior tongue rises slightly followed by a wave of glossal contraction, moving the jaw in an anterior-superior direction and elevating the posterior tongue and soft palate. This tongue elevation generates a positive pressure that transports the fluid towards the esophagus. This tongue elevation separates the anatomical system into two cavities, the first containing the nipple and the infant's mouth, and the second the oropharynx and the recently expressed fluid. The nasal cavity and lungs are sealed off by the palate and epiglottis, laryngohyoid complex, and arytenoids. Milk in the oropharynx is then evacuated out into the esophagus and stomach as the tongue contraction proceeds, bringing the back of the tongue up into contact with the hard palate, and decreasing the volume in the oropharynx. At this point, the oropharyngeal anatomy has returned to its initial resting position, and the pressure has returned to the baseline level, in preparation for an additional cycle of expression.

The complete cycle of expression lasts approximately 0.75 seconds, with the positive pressure phase occurring from 0-0.25 s, and the negative pressure occurring from 0.25-0.75 s, but times can vary greatly between infants, and within infants at different ages. Rate of sucking can be increased to increase efficiency. In addition, magnitude of tongue depression can be modulated to increase efficiency as infants increase in expertise and age. The cycle begins again with anterior tongue movement beginning prior to the completion of the previous elevation of the posterior tongue. The cycle tends to include sucking, swallowing, and breathing in a 1:1:1 ratio relative to the total cycle time. In general, the jaw depression occurs more slowly than the elevation. In addition, there are differences between nutritive and non-nutritive sucking. During nutritive sucking, the magnitude of lower jaw depression of the posterior tongue is greater than non-nutritive sucking, and occurs more slowly. In addition, non-nutritive sucking occurs at a significantly faster rate. In humans this manifests as a mean sucking rate of 88.9 sucks/min compared to the mean nutritive sucking of 74.0 sucks/min. Finally, an infant might modulate between nutritive and non-nutritive sucking multiple times during one feeding session. The ability to modulate sucking cycles in this way can have a great impact on the efficiency of fluid expression during each nursing session. While current devices can allow for a user-initiated or temporal triggered switch between the nutritive and non-nutritive expression cycles, no current devices have the capability of automatically switching between the cycles based on fluid expression parameters.

Figure 1B:
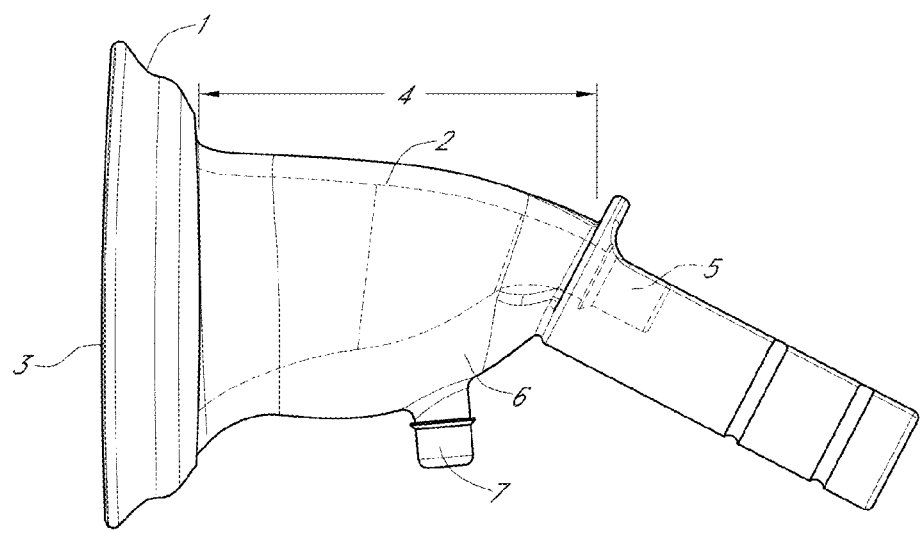
FIG. 1B is a side view of a biomimetic designed structure for use with a fluid expression device showing the single contiguous structure housed within a rigid external housing, according to some embodiments of the invention.

In some embodiments, disclosed herein is a biomimetic device to be used with a fluid expression device for biological fluid expression, including, but not limited to, the expression of breast milk in nursing mothers as seen in FIGS. 1A-B, illustrating anterior perspective and side views, respectively. The device is configured to, in some embodiments, improve expression efficiency, improve comfort, decrease noise, and/or improve portability in such a way that the biomechanics and fluid dynamics of natural breastfeeding are retained. In addition, some embodiments incorporate, one, two, or several environmental sensors to automate device function and to monitor variables related to pumping and breastfeeding health, a mobile application and wireless control capabilities, and an online data analysis portal and social network to improve the pumping experience.

The detailed description refers to the figures as necessary, in which like element numerals refer to like elements throughout the figures. The figures described below visualize many, but not all, aspects of embodiments of the described invention. In addition, alternative embodiments of the devices are described in the text relative to the figures. Some non-limiting examples of significant and major improvements to current pump design contained in some embodiments can include, for example, one or more of a unique structure of the device, mechanism of fluid expression, the automation of pump parameters based on device quantification, the inclusion of wireless connectivity and control via smartphone and tablet technology, and/or the use of a web portal for personal and comparative analysis.

In some embodiments, disclosed are systems and methods for a fluid expression device to be used for, but not limited to, the expression of fluid from mammals, including humans. Some embodiments differ from previous devices in the field in that they do not necessarily employ the typical breastshield assembly with rigid funnel-shaped breastcups, nipple tube, and receptacle, and the high power vacuum head generated negative pressure expression, and instead leverage biomimicry of infantile suckling to modify the structure and mechanics of the fluid expression system resulting in increased efficiency, increased comfort for the nursing mother, and employing a smaller and quieter design profile.

To this end, FIGS. 1-16 portray various embodiments in an assembly that discards the typical breast cup and nipple tunnel, and replaces it with a single, contiguous, and/or patent (e.g., having at least one channel allowing fluid flow therethrough from the proximal end to the distal end) structure 1 made of a soft flexible material capable of controlled asymmetrical collapse if necessary. The soft flexible material can include, for example, silicone rubbers or any other polymeric material ranging in durometer from Shore00-10 to ShoreA-70. The material thickness can vary both circumferentially and longitudinally and is designed such that upon loading with negative pressure fluctuation, the device mimics the biomechanics of a suckling infant.

FIGS. 1A-B portray one embodiment of the device including a patient interface which can be a soft, contiguous, patent patient interface structure 1 housed within a housing, such as a rigid housing 2. The rigid housing can, in some embodiments, range in durometer between Shore A 30-ShoreA 90, and/or simply be more rigid than the soft structure 1. The soft structure 1 includes a proximal end 3, an oropharyngeal portion 4, and a distal end 5 which can have a smaller, such as a significantly smaller diameter opening than the proximal end. In some embodiments, the distal end 5 opening diameter can be about or at least about 5%, 10%, 15%, 20%, 25%, 30%, 35%, 40%, 45%, 50%, or more smaller relative to the proximal end 3 opening diameter. The soft structure 1 is shown in this embodiment to be molded into a partially elevated position, such that a cavity 6 exists between the soft structure 1 and the rigid housing 2. The soft structure 1 can be deformed into this cavity 6, taking the shape of the cavity 6, when a negative pressure is applied through the negative pressure port 7. In order to maintain a proper seal between the soft, contiguous structure 1 and the rigid external housing 2, the soft structure may be molded with a gasket, ring, or lip to seal and wrap around the proximal and distal ends of the rigid housing as shown in FIGS. 1A-1B. In addition, the pieces can be co-injection molded together into one contiguous piece to maintain a seal. Further embodiments can include any additional methodology of maintaining a seal.

Figure 2A:
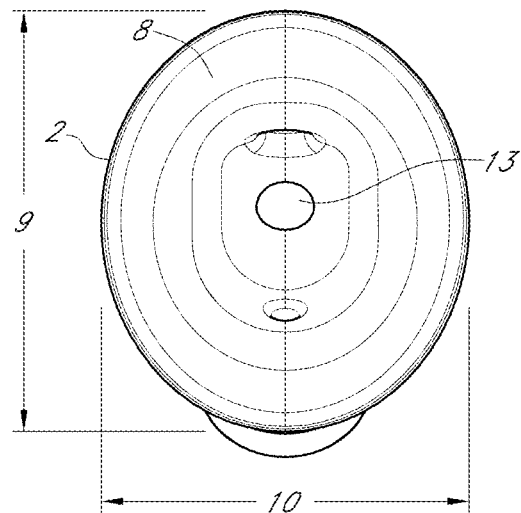
FIG. 2A is an anterior view of a biomimetic designed external rigid housing for use with a fluid expression device showing the shape of the proximal opening as well as the designed constraints of the body of the housing to restrict movement of the soft, contiguous structure housed within it (not pictured), according to some embodiments of the invention.
Figure 2B:
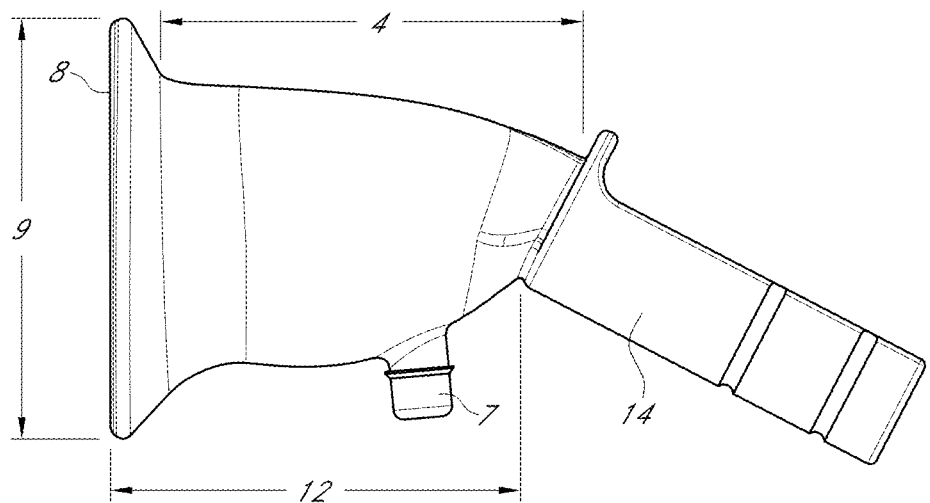
FIG. 2B is a side view of a biomimetic designed external rigid housing for use with a fluid expression device showing various aspects of the design which help create the proper biomimetic function, according to some embodiments of the invention.
Figure 2C:
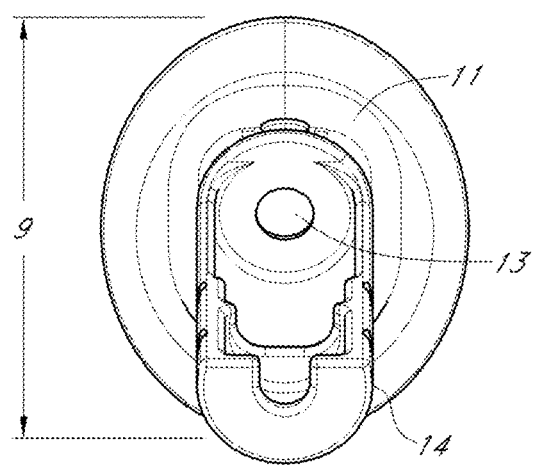
FIG. 2C is a posterior view of a biomimetic designed external rigid housing for use with a fluid expression device, according to some embodiments of the invention.

FIGS. 2A-C illustrate views of one embodiment of the rigid external housing 2. FIG. 2A portrays a frontal view of the rigid external housing 2. The proximal opening of the external rigid cup 8 can take an ellipsoid shape to approximate the opening of a child's mouth during suckling. In the illustrated embodiment this ellipsoid shape can be molded with the major axis in the vertical dimension 9 and the minor axis 10 in the horizontal dimension. This proximal elliptical opening 8 extends in some cases only generally over the nipple-areola complex, thereby minimizing the amount of breast tissue that is subjected to suckling pressure to that similar to breastfeeding. More specifically, some embodiments can include a major axis 9 in the vertical dimension of about 55 mm in diameter and a minor axis 10 in the horizontal dimension of about 50 mm in diameter resulting in a ratio of the major 9 to minor 10 axes length ratio of 1.1:1. Some embodiments include a major 9 axis in the range of between about 10 mm and about 100 mm in diameter oriented along the vertical axis of the structure (or between about 20 mm and about 80 mm, or between about 40 mm and about 65 mm in some embodiments), and a minor 10 axis in the range of between about 5 mm to about 80 mm in diameter oriented along the horizontal axis of the structure (or between about 15 mm and about 75 mm, or between about 35 mm and about 60 mm in some embodiments). In some embodiments, the ratio of the major axis 9 length to minor axis 10 length ratio can be, for example, about, at least about, or no more than about 1.02:1, 1.05:1, 1.08:1, 1.1:1, 1.15:1, 1.2:1, 1.25:1, 1.3:1, or more. Additional embodiments can include ellipsoid openings aligned with any axis depending on the desired clinical result. In some embodiments, proximal end openings having circular or other non-ellipsoid geometries are also possible. In some embodiments, the proximal end opening is sized and configured to receive a nipple-areola complex per se, but not the entire breast or substantially the entire breast, which advantageously allows for a more compact device. In some embodiments, the proximal end opening can cover a surface area of tissue of about or no more than about 10,000, 9,500, 9,000, 8,500, 8,000, 7,500, 7,000, 6,500, 6,000, 5,500, 5,000, 4,500, 4,000, 3,500, 3,000, 2,500, 2,000, 1,500, or less square millimeters.

The ellipsoid shape can advantageously mimic the gape of an infant's mouth during breastfeeding. This allows the device to engage similar breast tissue as that engaged by a nursing infant providing a more comfortable pumping experience by targeting the pressure of fluid expression to the appropriate anatomy. In addition, the sensation associated with engaging the nipple-areola complex in the same way as a nursing infant aids in stimulation of hormonal secretion and lactogenesis, thereby, increasing efficiency.

In addition to the ellipsoid shape of the proximal opening, in some embodiments the superior aspect of the oropharyngeal portion 11 of the external rigid housing 2 is molded into a parabolic shape with a slight indentation such that the soft structure 1, when housed inside the external rigid housing 2, is constrained in the superior region, allowing deformation to occur asymmetrically in the inferior direction. Not to be limited by theory, asymmetric deformation, described in more detail below, offers a method of negative pressure generation that allows a soft liner to mimic the tactile stimulation and pressure generation seen in the biomechanics of an infant's tongue. This can clinically manifest in greater stimulation of the hormonal response as well as limiting collapse of the superior surface of the liner which can be painful, and which, in cows, has been shown to cause severe teat end damage, thereby impacting the quality of milk.

FIG. 2B illustrates one embodiment of the rigid external housing. In this embodiment, the inferior oropharyngeal portion 12 of the rigid external housing is molded into a shape such that the inferior aspect approximates the anatomy of a child's oropharyngeal cavity in the tongue-depressed position during breastfeeding. This shape can be modified to offer a variety of different forms that the soft structure 1 will be deformed into. The distal end of the rigid external housing is comprised of a hole 13 through which the soft structure 1 exits the housing as well as a conduit 14 that can house a variety of one-way valves or insertions for a receptacle as seen in FIG. 2C. In addition, FIG. 2B portrays the pressure port 7 through which, in the present embodiment, a linear actuator will draw with negative pressure the soft structure 1 from its resting position into the cavity 6 of the external housing 2. FIG. 2C offers a posterior view of the rigid external housing 2, with a view of the hole 13 through which the soft structure 1 exits the housing. The conduit 14 in the foreground is shown in this embodiment as a hollow half cylinder capable of holding a one-way valve. This conduit 14 can, in some instances, be molded as a connection to a receptacle or to a hose leading towards a receptacle.

Figure 3A:
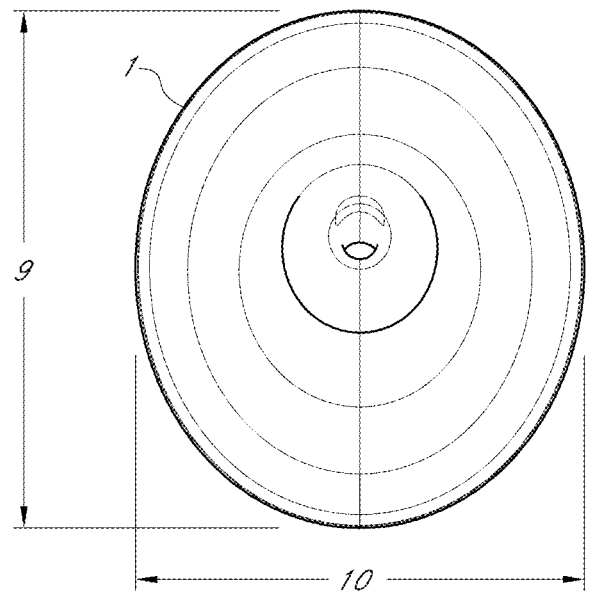
FIG. 3A is an anterior view of the elliptical proximal opening of the patent, contiguous structure with a major and minor axis, according to some embodiments of the invention.
Figure 3B:
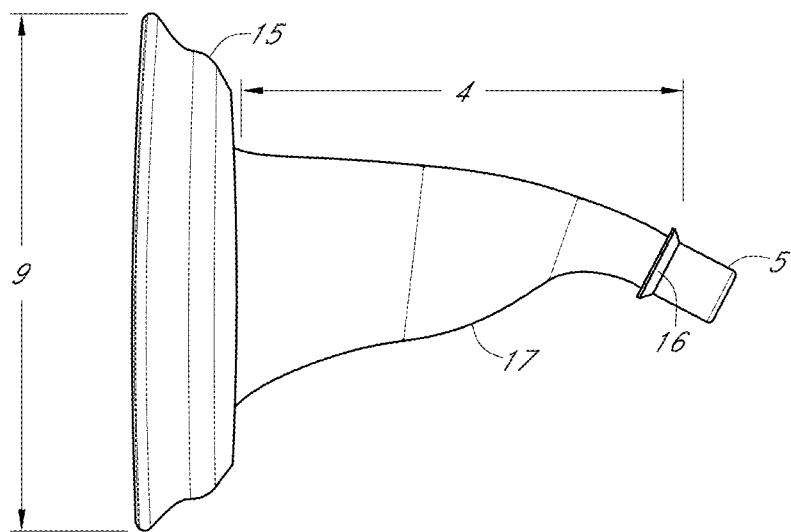
FIG. 3B is a side view of the single, contiguous patent structure with the major axis of the elliptical proximal opening and the shape of the inferior aspect of the oropharyngeal portion shown in some embodiments. Additionally, the proximal lip and distal disk are shown, which ensure a proper seal with the rigid housing.
Figure 3C:
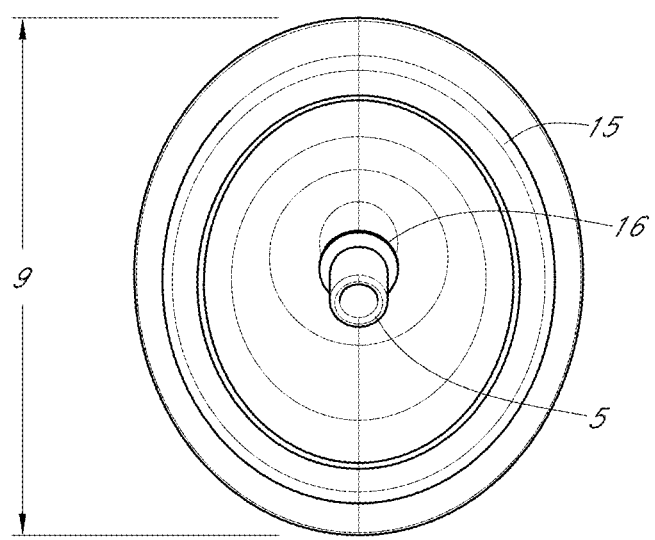
FIG. 3C is a posterior view of the distal opening of the patent, contiguous structure with a smaller diameter opening capable of attachment to a receptacle and/or to a vacuum source, according to some embodiments of the invention.

FIGS. 3A-C show an anterior, side, and posterior view, respectively, of the soft, contiguous structure 1. In this embodiment, the elliptical shape of the proximal opening is again oriented such that the major axis 9 is in the vertical dimension and the minor axis 10 is in the horizontal dimension to mimic the shape of an infant's lips when breastfeeding. In this embodiment, the soft structure 1 maintains its thickness throughout the oropharyngeal portion 4 as seen in FIG. 3B. In addition, the inferior aspect of the oropharyngeal portion 4 is molded in a partially elevated position along its length such that when subjected to negative pressure from the actuation mechanism, the inferior border of the soft structure 1 is movable and drawn downward (inferiorly) to generate negative pressure within the structure for fluid expression. This resting position of the molded soft structure can be modified to accommodate any linear actuation mechanism such that some embodiments might be molded in a fully depressed state and actuated using positive pressure, while others can be molded in a fully elevated state and actuated using negative pressure. These embodiments can be designed to emulate the asymmetrical biomechanics of a nursing infant to improve efficient fluid expression while remaining comfortable to the user. FIG. 3B portrays both the anterior portion of the soft structure 1 as a folded lip 15 used to seal the space between the soft structure 1 and the rigid external housing 2. This folded lip 15 can vary in thickness and form to optimize the seal of the negative space between the two structures. Similarly, FIG. 3C shows a broadened portion of the distal aspect of the soft structure 1 and creates a smaller ring 16 that is used to seal the posterior portion of the soft structure 1 as it exits the rigid external housing 2.

Figure 4A:
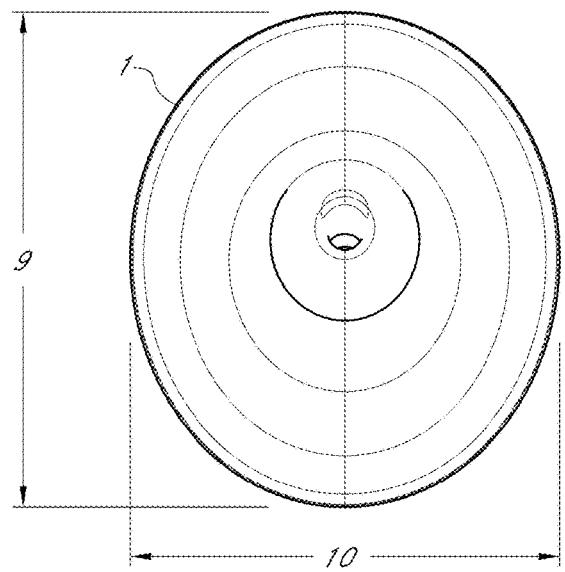
FIG. 4A is an anterior view of the soft, contiguous structure housed within the rigid external housing portraying the major and minor axes of the ellipsoid shape of both structures, according to some embodiments of the invention.
Figure 4B:
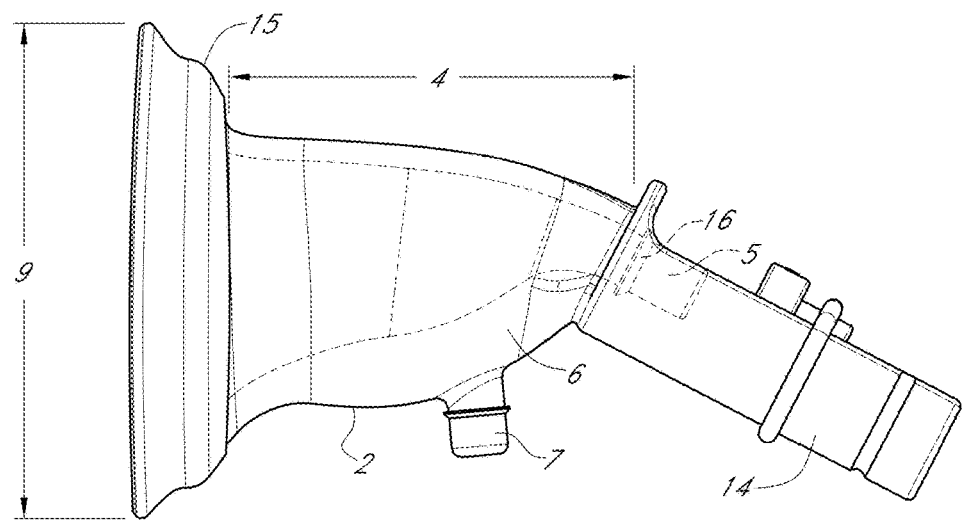
FIG. 4B is a side view of the soft, contiguous structure housed within the rigid external housing portraying the seal of the proximal lip and distal disk. Additionally, the inferior shape of the soft structure within the housing reveals the cavity that the soft structure will be drawn down into via negative pressure actuation delivered through a negative pressure port, according to some embodiments of the invention.
Figure 4C:
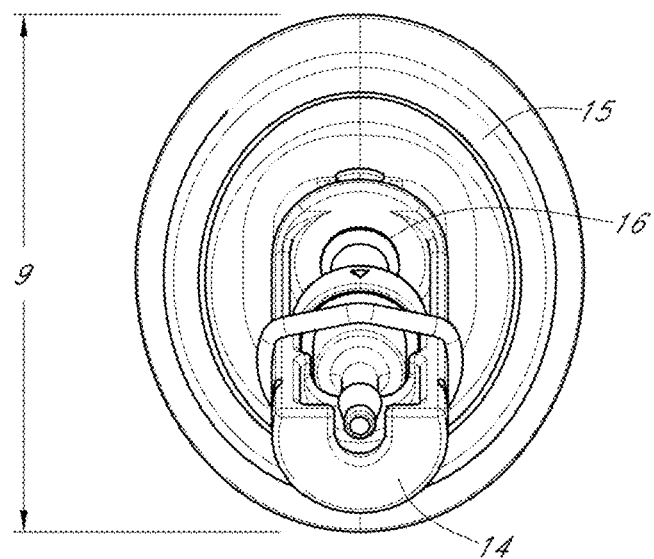
FIG. 4C is a posterior view of the soft, contiguous structure housed within the rigid external housing portraying the posterior seal between the two structures, according to some embodiments of the invention.

These two sealing points can be seen more clearly in FIGS. 4A-C. FIG. 4A portrays the elliptical shape of both the soft structure 1 and the external rigid housing 2 mimicking the shape of an infant's mouth during breastfeeding. FIG. 4B shows a side view of the two structures, portraying the proximal lip 15 and the distal ring 16 that generates a seal between the soft structure 1 and the external rigid housing 2 creating a cavity 6 within the two structures which the soft structure 1 is drawn down into, in the current embodiment, by the actuation mechanism. The linear actuation is transmitted, in this embodiment, pneumatically via the pressure port 7. FIG. 4C portrays the ring 16 on the external surface of the external rigid housing 2 where the soft structure 1 exits the housing. In this current embodiment, the conduit 14 is housing a one-way valve and leads to the fluid receptacle (not pictured here).

Alternative embodiments of the soft, contiguous structure 1 and the rigid external housing 2 can also be employed to achieve similar functionality. For example, FIGS. 5A-F portray the soft, contiguous structure 1 in a different morphology. The proximal, elliptical opening extending in some cases only over the nipple-areola complex, and a variable material thickness of the inferior 17, lateral 18, 19, and superior 20 aspects of the oropharyngeal portion 4 are noted. In addition, a ridge 21 can be present to facilitate actuation of the inferior aspect 17 of the structure 1. The densities of the material, which can be modulated by properly designing the molds and polymer mixtures and chemistry when casting this structure, can also vary along the length of the pieces as necessary to offer variable mechanical properties to specific portions of the structure.

Figure 5A:
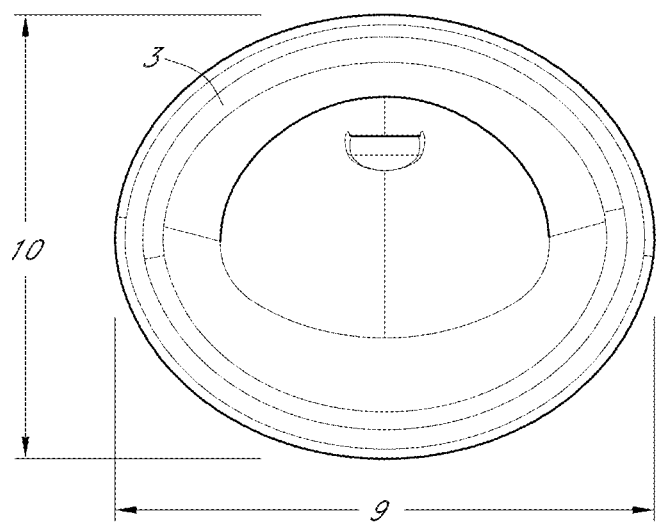
FIG. 5A is an anterior view of the elliptical proximal opening of the patent, contiguous structure with a major and minor axis, according to some embodiments of the invention.
Figure 5B:
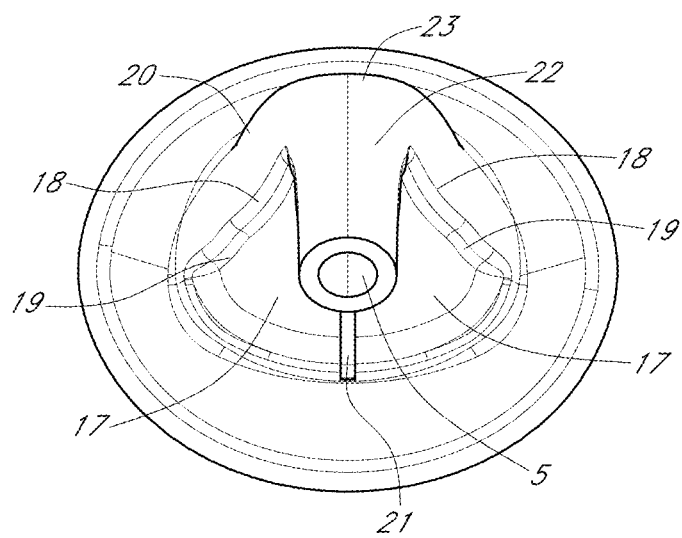
FIG. 5B is a posterior view of the distal opening of the patent, contiguous structure with a smaller diameter opening capable of attachment to a receptacle and/or to a vacuum source, according to some embodiments of the invention.
Figure 5C:
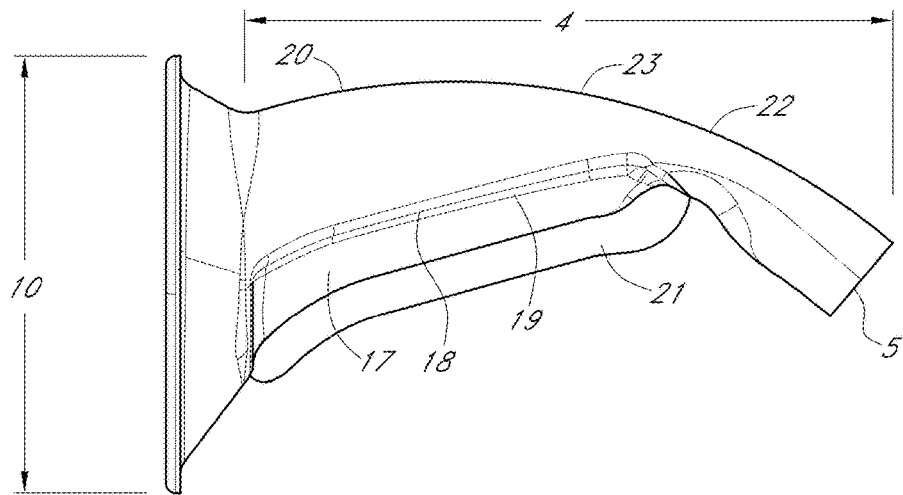
FIG. 5C is a side view of the single, contiguous patent structure with the minor axis of the elliptical proximal opening shown in some embodiments.
Figure 5D:
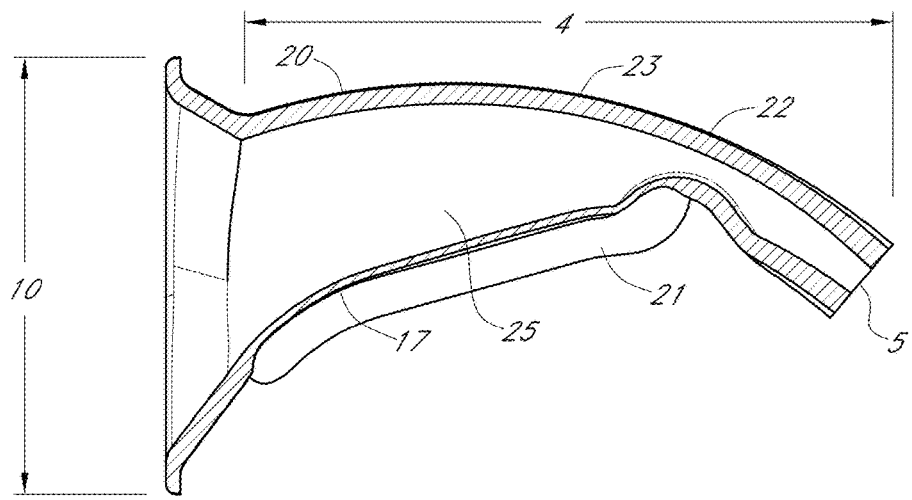
FIG. 5D is a sectioned side view of the single, contiguous patent structure.
Figure 5E:
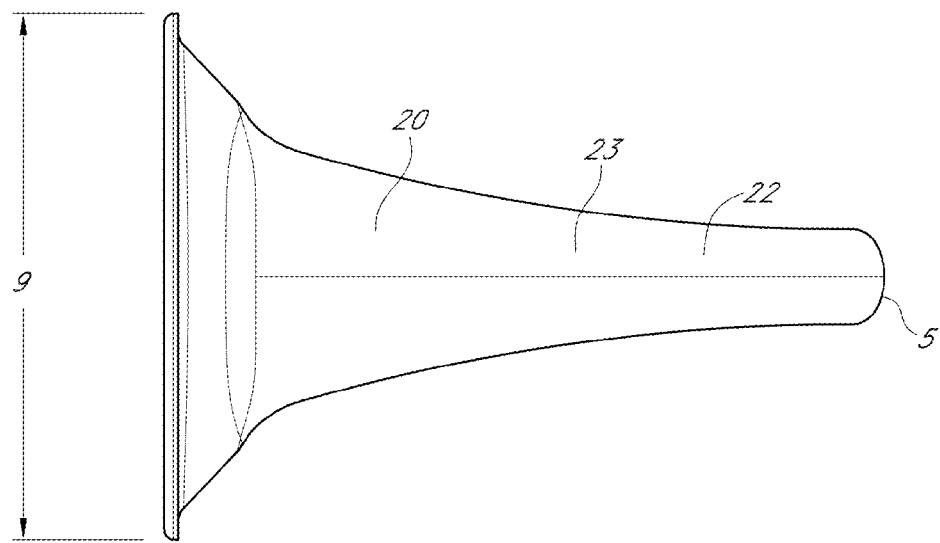
FIG. 5E is a top view of the single, contiguous, patent structure.
Figure 5F:
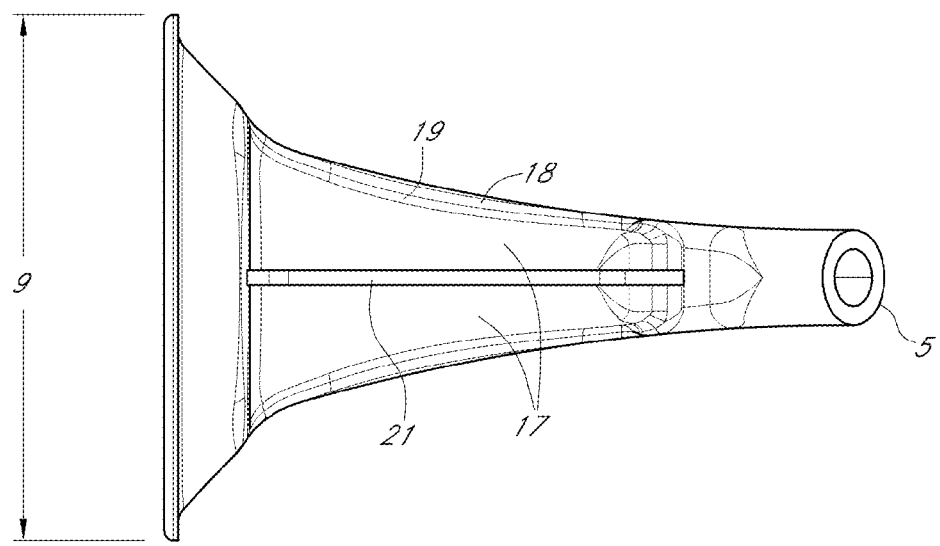
FIG. 5F is bottom view of the single, contiguous, patent structure.
Figure 6A:
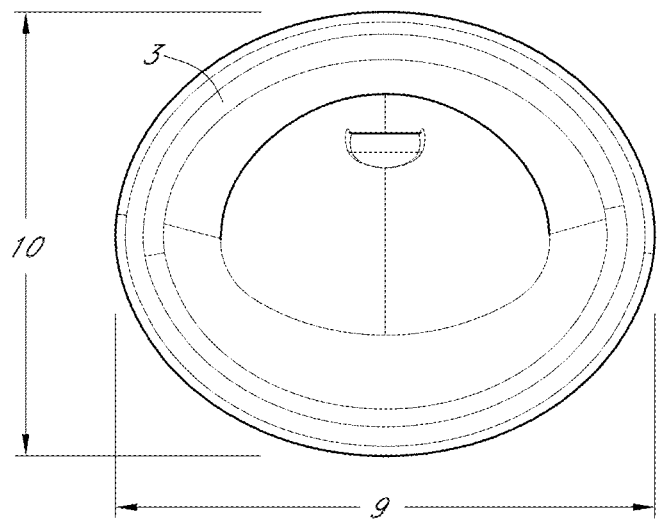
FIG. 6A is a front view of an embodiment of the structure where the stiffening of the hard palate is achieved using a separate component, adhered to the superior aspect of the oropharyngeal portion of the soft, contiguous structure.
Figure 6B:
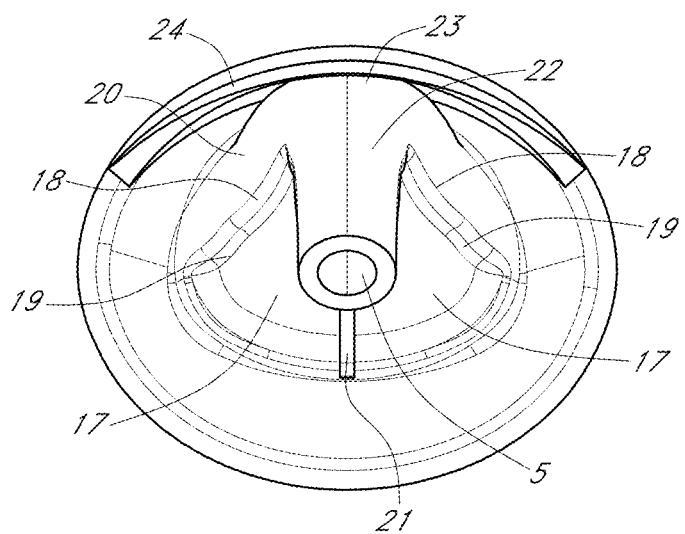
FIG. 6B is posterior view of an embodiment of the structure where the stiffening of the hard palate is achieved using a separate component, adhered to the superior aspect of the soft, contiguous structure.
Figure 6C:
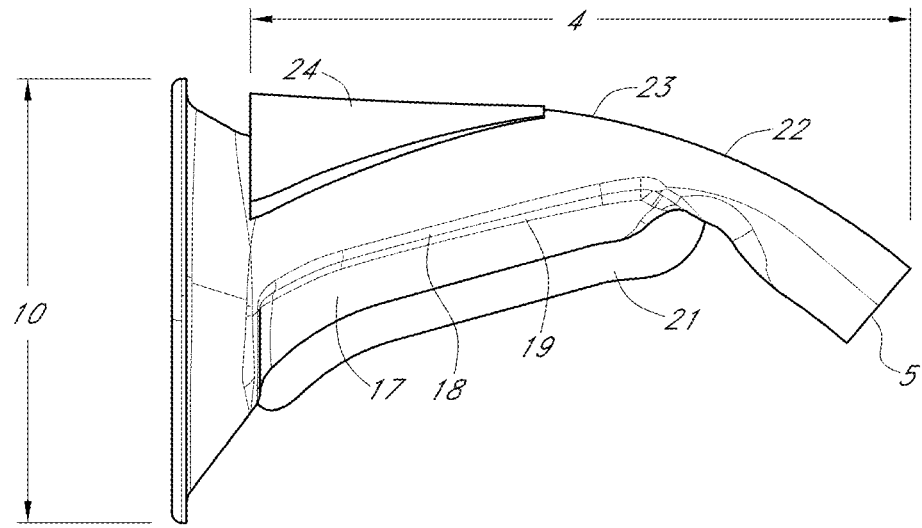
FIG. 6C is a side view of an embodiment of the device where the stiffening of the hard palate is achieved using a separate component, adhered to the superior aspect of the soft, contiguous structure.
Figure 6D:
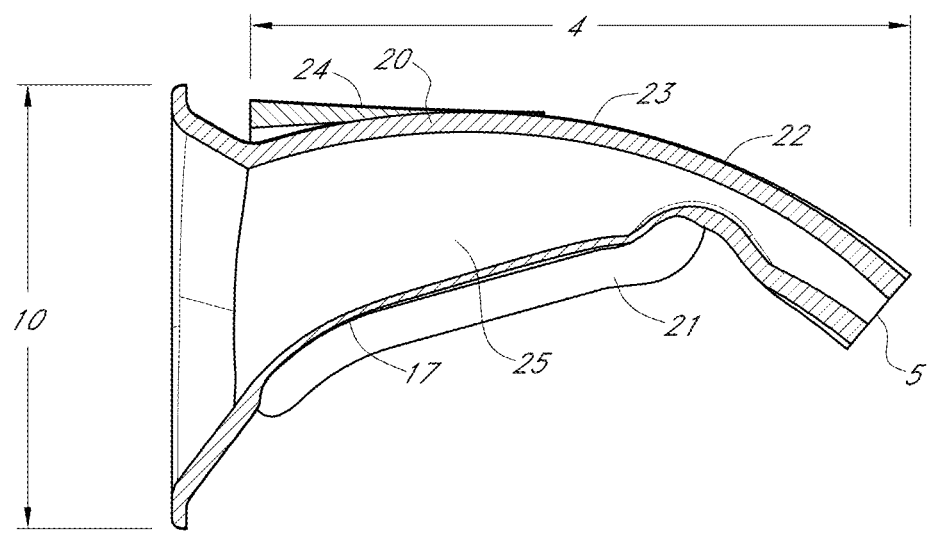
FIG. 6D is a sectioned side view of an embodiment of the device where the stiffening of the hard palate is achieved using a separate component, adhered to the superior aspect of the structure.
Figure 6E:
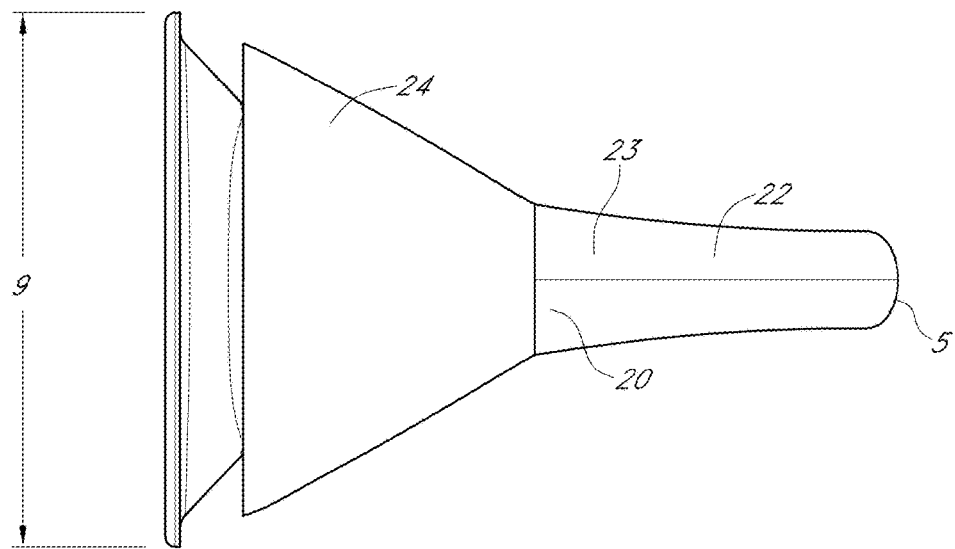
FIG. 6E is top view of an embodiment of the structure where the stiffening of the hard palate is achieved using a separate component, adhered to the superior aspect of the soft, contiguous structure.
Figure 6F:
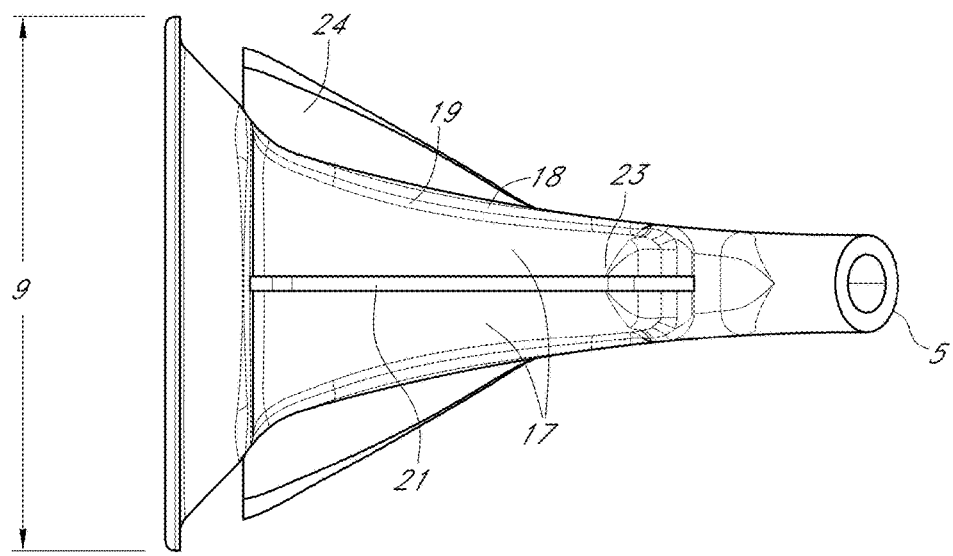
FIG. 6F is a bottom view of the single, contiguous patent structure with the stiffening component portrayed above.

More specifically, the proximal end can include an ellipsoid opening with a major 9 and minor axis 10 as shown in FIGS. 5A and 6A. Some embodiments can include a major axis 9 in the horizontal dimension of about 55 mm in diameter and a minor 10 axis in the vertical dimension of about 50 mm in diameter resulting in a ratio of the major 9 to minor 10 axes length ratio of 1.1:1. As previously noted, some embodiments include a major 9 axis in the range of 10-100 mm in diameter oriented along the horizontal axis of the structure, and a minor 10 axis in the range of 5-80 mm in diameter oriented along the vertical axis of the structure, or other dimensions, some of which are disclosed elsewhere herein. In some embodiments, the ratio of the major axis 9 length to minor axis 10 length ratio can be, for example, about, at least about, or no more than about 1.02:1, 1.05:1, 1.08:1, 1.1:1, 1.15:1, 1.2:1, 1.25:1, 1.3:1, or more. Additional embodiments can include ellipsoid openings aligned with any axis depending on the desired clinical result. In some embodiments, proximal end openings having circular or other non-ellipsoid geometries are also possible. In some embodiments, the proximal end opening is sized and configured to receive a nipple-areola complex per se, but not the entire breast or substantially the entire breast, which advantageously allows for a more compact device. Again, this ellipsoid structure can be configured to engage a similar amount of breast tissue as a nursing infant and to avoid engaging breast tissue that is not engaged during breastfeeding. This structural difference between certain embodiments of the present design and previous devices allows the pressure profile to be limited to the nipple-areola complex. This avoids the application of pressure to the surrounding breast tissue, reducing the need push one's breast into a constrained nipple tunnel and reducing the pulling of excess tissue into the breastshield.

The oropharyngeal portion 4 of the structure 1 can be designed to allow variable material thicknesses circumferentially around the axial cross-section of the oropharyngeal portion 4 as seen in FIGS. 5B-F. This variation in thickness is designed such that the most inferior aspect 17 of the structure 1 is the thinnest, while the most superior aspect 20 of the structure 1 is the most thick, and thereby the most stiff. The gradation of thickness increases as one moves from the inferior floor 17 of the structure 1 along the lateral wall 18 and 19 and up to the superior area 20. In this way, the inferior aspect 17 of the structure 1 offers the greatest flexibility and ease of collapse, thereby mimicking the motility of the infantile tongue. In some embodiments, the following degree measurements generally correlate to sectors along a clock face, with 0° or 360° being at the superior-most 12 o'clock position, 90° being at the lateral 3 o'clock position, 180° being at the inferior-most 6 o'clock position, and 270° being at the lateral 9 o'clock position. This region of the structure can, in some embodiments extend circumferentially up to 90° to 270° at the largest range. The lateral aspects 18 & 19 mimic the motility and stiffness of the buccal mucosa offering slightly stiffer and less collapsible portions of the structure 1 when compared to the inferior aspect 17. The more inferior lateral aspect 19 can range between 45°-135° on one side of the structure and between 225°-315° on the opposite side of the structure at the largest range. The more superior lateral aspect 18 can range between 0°-100° on one side of the structure and 260-360° on the opposite side of the structure at its largest range. The variable circumferential thickness of the walls can encompass a wide variety of ranges and combinations that can ensure a controlled asymmetrical collapse and actuation. Some embodiments can include a superior 20 aspect with a material thickness of between about 1-5 mm, an incremental decline in the thickness of the lateral wall with a thicker portion 18 having a thickness of between about 0.8-3 mm, and a thinner 19 portion having a thickness between about 0.6-2 mm, and the thinnest inferior portion 17 having a thickness between about 0.2-0.9 mm. In this way, some embodiments might include a relative material wall thickness from superior to lateral to lateral to inferior of 100%, 75%, 50%, to 25%, respectively, in either a stepwise or gradual fashion, or a combination of the foregoing allowing for variances in the relative percentages of up to about 1, 2, 3, 4, 5, 6, 7, 8, 9, or 10% in either direction at any wall positioning. The configuration advantageously allows the structure responds to the baseline pressure in such a way that a controlled, but passive, asymmetrical collapse around the nipple occurs. Similarly, the variable thickness is intended to facilitate the asymmetrical deformation of the liner down towards the rigid external housing 2 during actuation. The asymmetric actuation of the liner can be important in some embodiments for pump efficacy and comfort. The ability to modulate pressure with the deformation of a soft liner has been shown to increase hormonal secretions in nursing mothers when compared to rigid breastshields. However, a radially collapsing and expanding liner can result in discomfort and in some cases tissue damage. By collapsing and expanding the liner in an asymmetric fashion, the nipple in some embodiments is never or rarely constricted by the liner; however, some tactile stimulation is provided to the inferior aspect of the nipple-areola complex. Finally, the superior surface 20 mimics the stiffness of the hard and soft palate in the anterior and posterior regions, respectively. To achieve the difference between the hard and soft palate, the superior aspect 20 of the oropharyngeal portion 4 can decrease in thickness longitudinally in a stepwise or gradual fashion, or a combination of the foregoing to match the flexural stiffness of the hard and soft palate, respectively. The posterior superior surface 22 of the structure 1 in FIGS. 5 & 6, mimics the soft palate, and can therefore be thinner than the anterior superior surface 20 of the structure 1, which is the thickest and most stiff portion of the oropharyngeal portion 4. In other words, in some embodiments, the structure 1 can have an axial cross-section with varying stiffness properties along the cross-section, such as a superior portion 20 which is stiffer than lateral portions 18 & 19 (which can include in some embodiments a first lateral portion having a first stiffness and a second lateral portion having a second stiffness that is less than the first stiffness), which is in turn stiffer than an inferior portion 17. The dimensions of the hard and soft palate portions of the structure 1 can be similar to those measured in infants of the species in question. In humans, the mean curvilinear length of the hard palate along the mid-sagittal plane is, in some cases, 28.87±3.9 mm. The mean length of the soft palate in human infants has been measured to be, in some cases, approximately 23.62±3.6 mm. The junction of the hard and soft palate 23 lies at the point of transition between these two thicknesses on the superior aspect of the soft, contiguous structure. While asymmetrical collapse can have significant advantages as noted herein, in some embodiments, structures can also be configured to collapse symmetrically to achieve milk expression (e.g., by having a constant or substantially constant stiffness from superior to lateral to inferior).

The dimensions of the soft, contiguous structure 1 that approximate the anatomy can in some cases match the average values measured in the academic literature. The diameters of the major 9 and minor 10 axes of the proximal opening 3 can lie within the range of infant lip measurements for each species. The area of the opening 3 of the structure 1 can also be sized based on the mean measurements of oral gape for each species where they exist. The length of the structure 1 can include two portions, from the proximal opening 3 to the junction between the hard and soft palate 23. The second portion is from the hard and soft palate junction 23 to the distal opening 5, corresponding to the distance to the esophagus. Some embodiments can also allow for the customization of these flexible, molded pieces based on medical imaging technologies, for example, but not limited to, ultrasonic measurement of lip diameter and oropharyngeal length and width of a particular infant. These measurements can be used to develop a mold specific to that infant, and a customized structure can be manufactured, such as via 3D printing in some cases. In some embodiments, dimensions can be measured by hand, either taken from measurements of the infant's oral gape, or from morphological measurements taken from the nursing mother's nipple and/or breast. This design can accurately position the hard-soft palate junction 23 such that the nipple, when received in the single, contiguous structure 1, will lie just proximal to the hard-soft palate junction 23, and the actuation of the flexible inferior aspect 17 of the oropharyngeal portion 4 will occur primarily at the axial position of the hard-soft palate junction 23, with some small actuation anterior to that position as well. The importance of mimicking the anatomy in some cases plays a large role in the efficacy of fluid expression as well as the comfort and associated lactogenesis. The structural elements such as the infant gape, hard palate, the hard-soft palate junction, and the variable thickness of the liner can be advantageous to tightly fitting the nipple-areola complex within the device in the same way that the nipple-areola complex fits into a baby's mouth. This tight fit allows a comfortable positioning of the nipple, while minimizing the dead air volume within the device. The subsequent asymmetrical actuation of the liner then provides the necessary pressure profile for comfortable and efficient fluid expression, without the risk of severe nipple elongation, duct collapse, and tissue damage. The tactile stimulation of the liner against the inferior aspect of the nipple is also thought to increase the hormonal secretion of the nursing mother resulting in increased milk supply and efficiency of fluid expression.

FIGS. 6A-F portray another embodiment that replaces the external rigid housing 2 and the variable thickness of the superior aspect described in FIGS. 5A-F with a separate stiffening component 24 that can be adhered to the superior surface 20 of the soft structure 1 to offer the stiffness of the hard palate. The nature of the connection between the stiffening component and the liner can include co-injection molding, bonding, or any other technique known to one with skill in the art. Similar stiffening components might be included to mimic the mandible and maxilla of the suckling infant to allow additional stiffening in those regions if deemed necessary to accurately mimic the suckling biomechanics. In some embodiments these components can include reinforcing rods, ribs, layers, or other elements. In some embodiments, the inferior 17, lateral 18 & 19, and/or superior portions 20 may be made of different materials or material combinations altogether, such as a coextruded zone or the like.

FIGS. 7-15 portray schematic representations of various embodiments of the fluid expression device associated with the soft, contiguous structure 1 and stiffening structures 2 or 24 described above. The novel mechanisms embodied by some embodiments disclosed herein can be designed to mimic the baseline pressure generated by an infant's diaphragm and the negative pressure modulation generated by the infant's tongue. The novel mechanisms within some embodiments disclosed herein do not utilize the typical high power vacuum head used in current devices to generate cycles of peak vacuum pressures to "suck" fluid from the nursing mother. Instead, some embodiments use a micro vacuum 26, typically a lower power head, but not limited to low power, combined with a pair of solenoid valves 27 & 28 to generate a continuous baseline mean pressure between, e.g., about −45 mm Hg to −80 mm Hg to match those measured during breastfeeding in suckling infants in humans. In other mammalian species, these vacuum requirements might vary, and the device and vacuum design can be modified accordingly. Upon placing the device over the mother's nipple-areola complex, and applying the baseline pressure, a physical latch can be generated. In the case that this latch is not sufficient for hands-free pumping, the user may need to hold the device in place. Alternatively, embodiments of the device can include a bra-insert to hold the device in place. Some embodiments can include shoulder and torso harnesses, or other strapping fabrics and mechanisms to hold the device in place to allow for hands-free expression. In addition, adhesives fabrics, such as, but not limited to, Geckskin™ (University of Massachusetts-Amherst, Amherst, Mass.), to leverage Van der Waals forces on the anterior surfaces of the soft structure 1 in FIGS. 3A & 4A to hold the device in place can be used. Also, some embodiments can include lubricating systems to prevent chafing after repeated uses. In some embodiments, the thicker lip shaped structures along the flange of the ellipsoid opening 15 can include small pores to allow for lubricating fluid to slowly leak upon the user's breast. This lubricating fluid might also serve as a source of wet adhesion to ensure a proper seal between the device and the user's breast. Some embodiments can include user-applied lubrication prior to use or no lubrication can be used.

Figure 7:
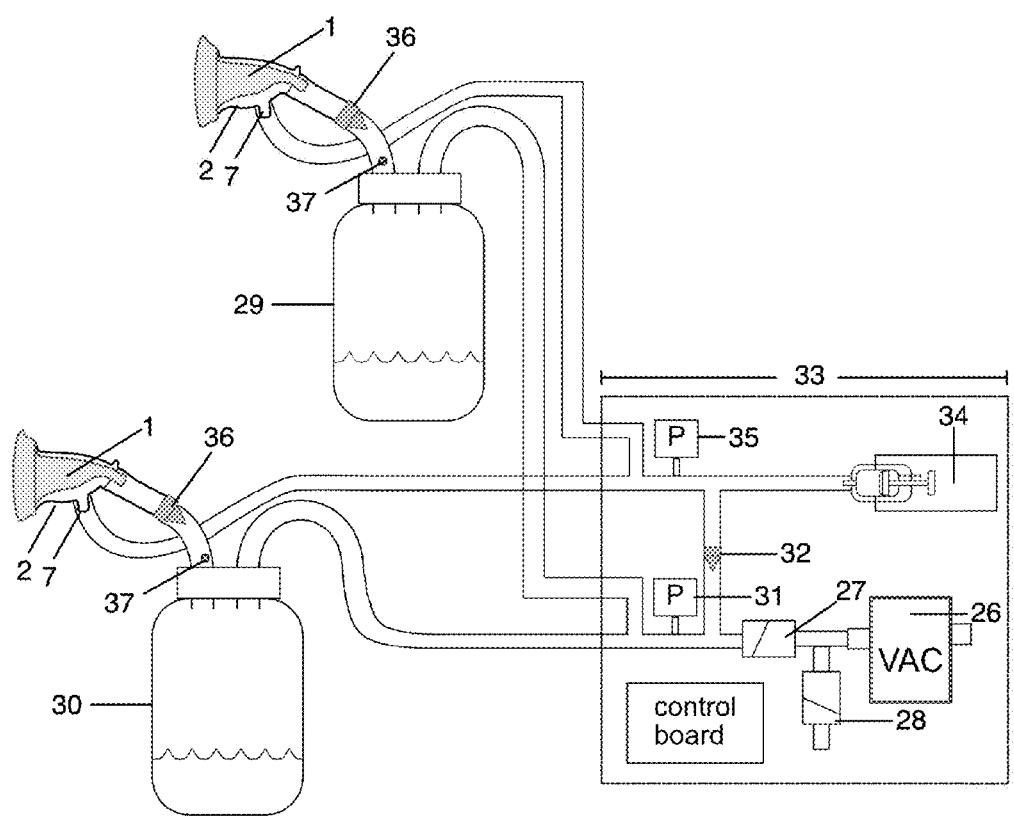
FIG. 7 is a schematic representation of one embodiment of the fluid expression device using a vacuum system to generate baseline pressure and an actuation mechanism to generate negative pressure inside the rigid external housing.

As seen in FIG. 7, baseline pressure can be transmitted from a vacuum 26, through a bottle 29 & 30 if necessary, or directly into the internal volume 25 of the oropharyngeal portion of the soft, contiguous structure 1. Thus, the device can apply a continuous baseline pressure using a vacuum 26, and solenoid valves 27 & 28, coupled directly to the internal volume 25 of the soft, contiguous structure 1. This vacuum 26, combined with the variable thickness of the soft, contiguous structure 1 can allow the asymmetrical collapse of the inferior aspect 17 (tongue) and lateral (buccal) aspects 18 & 19 of the oropharyngeal portion 4 of the structure 1 around the received nipple without constricting the nipple, and minimizing nipple movement during expression. In some embodiments, the solenoid valves are used to maintain the desired baseline pressure. One solenoid valve 27 can be open during baseline pressure generation, while the second solenoid valve 28, can be closed during baseline pressure generation. The pressure can be measured, for example, with a pressure transducer 31 placed inline with the baseline vacuum. Once the baseline pressure desired by the user has been achieved, one solenoid valve 27 will close while the other solenoid valve 28 will open, allowing the vacuum 26 to continue drawing air without further decreasing the pressure in the system. In some embodiments where asymmetrical collapse of the soft structure 1 is minimized, a connection containing a one-way valve 32 is placed within the console 33 between the vacuum 26 and the actuation mechanism 34 to equalize the pressure within the soft structure 1 and the rigid external housing 2. A second pressure transducer 35 is plumbed inline with the actuation mechanism 34 to measure the pressure within the external rigid housing 2. This baseline pressure simulates the latch that a nursing infant achieves using its diaphragm. The baseline pressure can help to achieve the peak pressures measured in nursing infants as well as to stimulate the hormonal response in the nursing mother.

Upon generation of baseline pressure, fluid expression can be achieved via negative pressure resulting from asymmetric deformation of the internal volume 25 of the oropharyngeal portion 4 of the soft, contiguous structure 1. Some embodiments of this asymmetric volume modification can use an actuation mechanism 34 to elevate and depress the inferior aspect 17 of the oropharyngeal portion 4 at the junction between the soft and hard palate 23. As seen in FIG. 7, this actuation would draw the inferior aspect 17 of the soft structure 1 down into the cavity 6 between the soft structure 1 and the rigid external housing 2. To minimize the volume of the pressure vessel being modified, some embodiments, as shown in FIG. 7, can include a one-way valve 36 at the junction between the distal opening of the structure 5 and the waiting receptacle 29 & 30 to allow for a smaller pressure vessel comprised primarily of the soft, contiguous structure 1 and the nursing breast. This valve 36 can be, but is not limited to, a micro one-way air check valve, a micro solenoid valve, a micro pneumatic valve, a micro air release valve, a micro-resistance ball type check valve, a micro one-way disc valve, a one-way poppet valve, a one-way pressure relief valve, a micro Tesla valve or valvular conduit, or a micro v-type flange ball valve. The valve 36 can be made of, for example, any lightweight plastic or metal.

In addition, a real-time sensor 37 is shown in FIG. 7. One, two, or more sensors 37 can be positioned anywhere on the external aspects of either the external rigid housing 2, hosing, or the receptacles 29 & 30 as described below. Sensors 37 can be used to send data to a software and/or hardware controller which in turn can analyze and/or output the displayed data or other information to users and care providers, or to modulate pump function to better optimize the system for each user. More detailed description of sensor use and function is described below.

The cycle frequency of the actuation mechanism can correspond to the various suckling cycles exhibited by mammalian infants. In humans, the cycle of tongue elevation and depression can in some embodiments operate in such a manner that the peak pressure magnitudes do not exceed those seen in vivo for each species. In humans this is a mean peak pressure of approximately −160 mm Hg, and the linear actuation can be calibrated not to exceed this pressure. For alternative species, the peak pressures can be calibrated to match those measured in vivo for each specific species. For example, in dairy calves, the suckling pressure is ~500 mm Hg. Cycle frequency and duty cycle can be programmed in combinations that match the measured cycle frequency and duty cycle for each species, such that the user cannot set combinations that will operate outside of the appropriate combinations of cycle frequency and duty cycle for the species from which fluid is being expressed. In humans, the cycle frequencies can, in some embodiments, be set to allow for duty cycles in the about one-half to about two-thirds range. Sucking cycles have been measured in about 0.75 seconds in some cases, with the positive pressure phase lasting about 0.25 seconds and the negative pressure phase lasting about 0.50 seconds. The negative pressure phase can be in some cases at least about or about 1×, 1.25×, 1.5×, 1.75×, 2×, 2.25×, 2.5×, 2.75×, 3×, or more longer in duration than the positive pressure phase. The elevation of the inferior aspect 17 of the soft, contiguous structure 1 operates more rapidly than the depression in some cases. Allowances can be made for differences in nutritive and non-nutritive sucking where nutritive sucking embodies larger magnitude tongue depression and slower cycling (approximately 74.0 sucks/min in humans compared to 88.9 sucks/min for non-nutritive sucking). The non-nutritive cycle plays a role in stimulating hormonal release in the nursing mother and triggering milk expression both during feeding bouts and over the longer term nursing period. In dairy calves, the cycle frequencies can, in some embodiments, be set to allow for duty cycles of approximately 120 sucks/min for nutritive sucking.

Figure 8A:
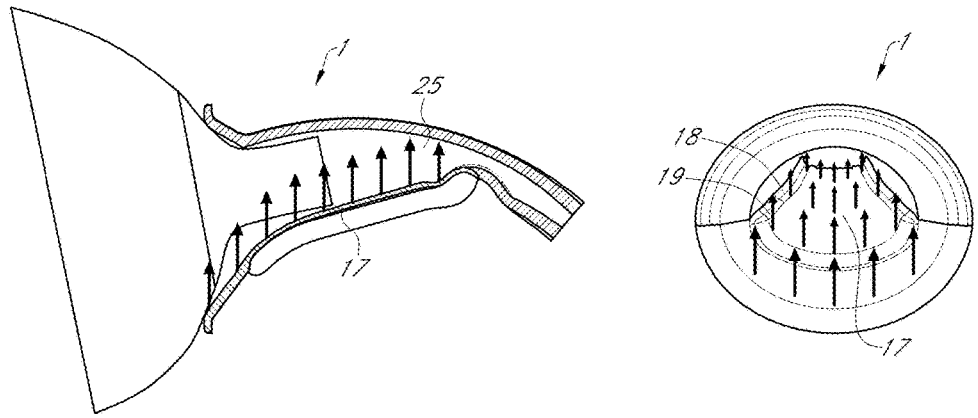
FIG. 8A is a schematic representation of the single contiguous structure at rest prior to the application of a baseline pressure in both a side view and anterior view.
Figure 8B:
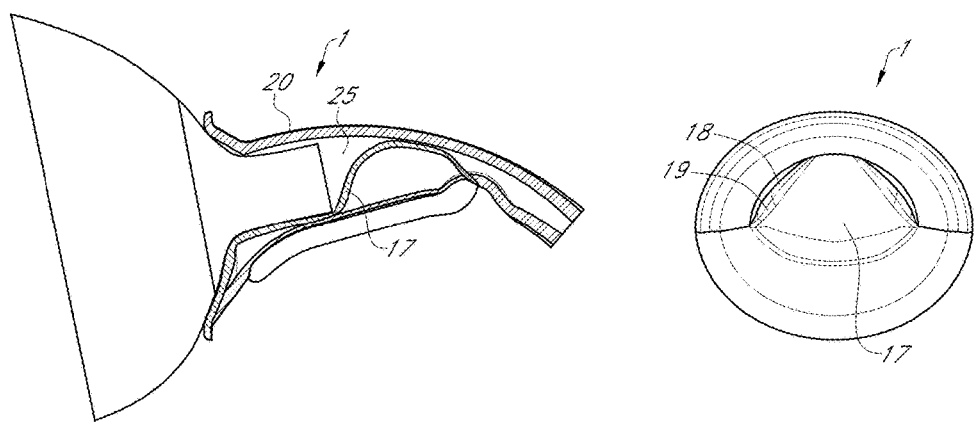
FIG. 8B is a schematic representation of the asymmetrical collapse of the internal volume of the single contiguous structure under a baseline pressure in both a side view and anterior view.

FIGS. 8A-8B illustrate the asymmetrical collapse of the soft, contiguous structure 1 when exposed to baseline vacuum, according to some embodiments. One purpose of the variable stiffness, both circumferentially and longitudinally along the superior aspect of the oropharyngeal portion 4 of the structure 1, is to ensure a proper asymmetrical collapse of the structure 1 upon the activation of constant, sub-atmospheric, baseline pressure as seen in FIG. 8. Asymmetrical collapse implies that, in some embodiments, the inferior aspect 17 collapses superiorly and the lateral aspects 18 & 19 collapse medially towards the nipple to minimize dead-air volume within the internal volume 25 of the oropharyngeal portion 4, in contrast with a hollow structure that collapses symmetrically, such as radially inwardly in some cases. FIG. 8A depicts the structure 1 in the rest position prior to the activation of the baseline pressure in both the side and anterior views. The inferior aspect 17 is in the resting position below the nipple, leaving dead air within the internal volume 25 of the structure 1. As a vacuum begins to draw a baseline pressure, the inferior aspect 17 and the lateral aspects 18 & 19 collapse asymmetrically towards the nipple without constricting it as seen in FIG. 8B. Therefore, the dead air volume within the internal volume 25 of the structure 1 is minimized. This collapse, however, does not impinge upon, or constrict, the nipple in any way in some cases. Additional embodiments can allow asymmetrical collapse in any direction, for example, the superior aspect 20 collapsing down towards the mandibular stiffening structures. In such embodiments, the variable thickness both radially and longitudinally will have to be adjusted to accommodate such a collapse. In some cases, however, the collapse does not occur symmetrically, or radially, from all sides. In some cases, the collapse can occur symmetrically.

Figure 9A:
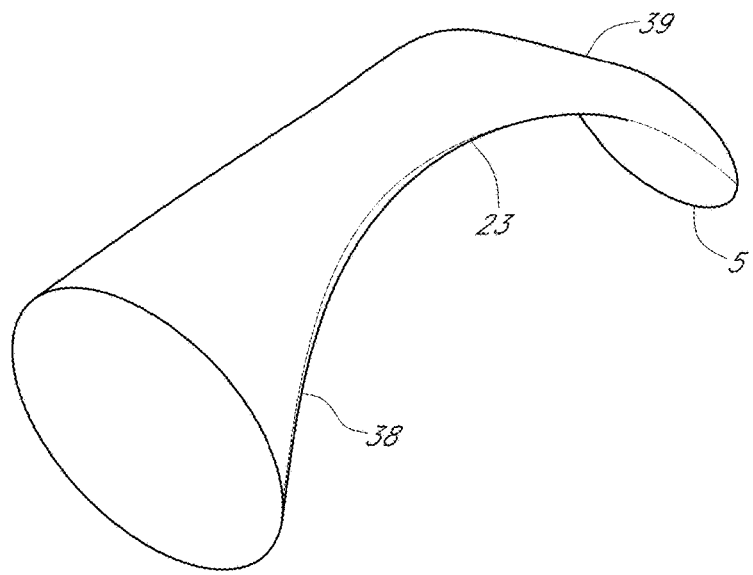
FIG. 9A is a perspective view of the single contiguous internal volume in a fully elevated position, where the inferior aspect has been actuated superiorly separating the anterior and posterior segments into two separate volumes, according to some embodiments.
Figure 9B:
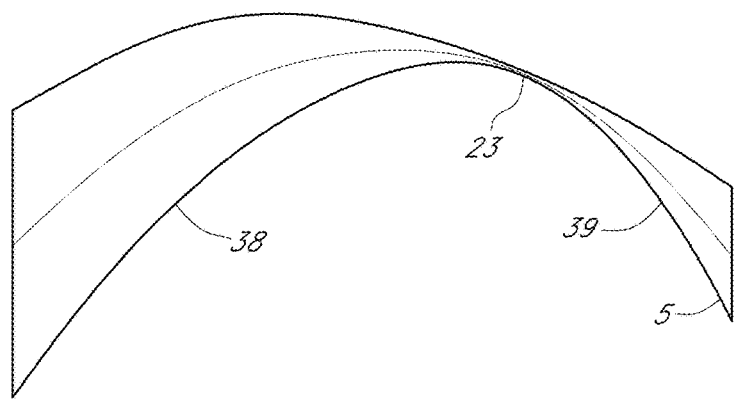
FIG. 9B is a side view of the single contiguous internal volume in a fully elevated position, where the inferior aspect has been actuated superiorly separating the anterior and posterior segments into two separate volumes, according to some embodiments.
Figure 9C:
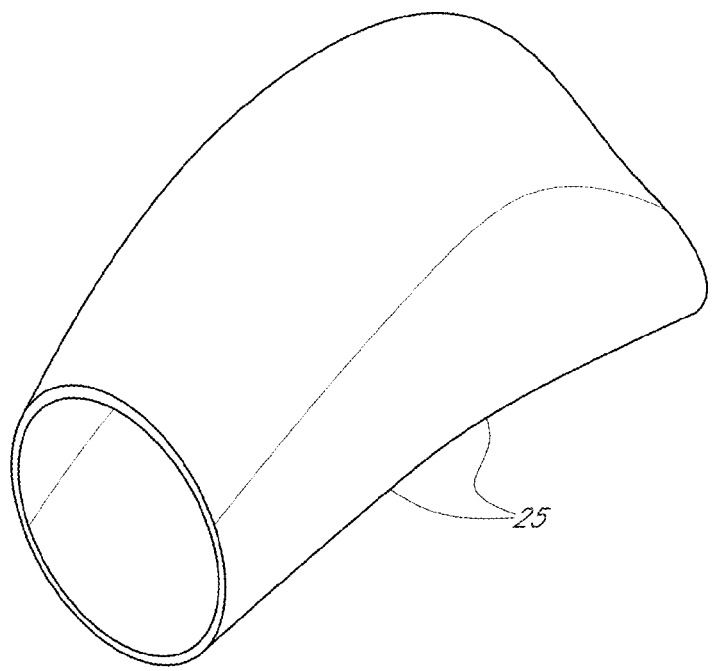
FIG. 9C is a perspective view of the single contiguous internal volume in a fully depressed position, where the inferior aspect has been actuated inferiorly modulating the volume into one large cavity, according to some embodiments.
Figure 9D:
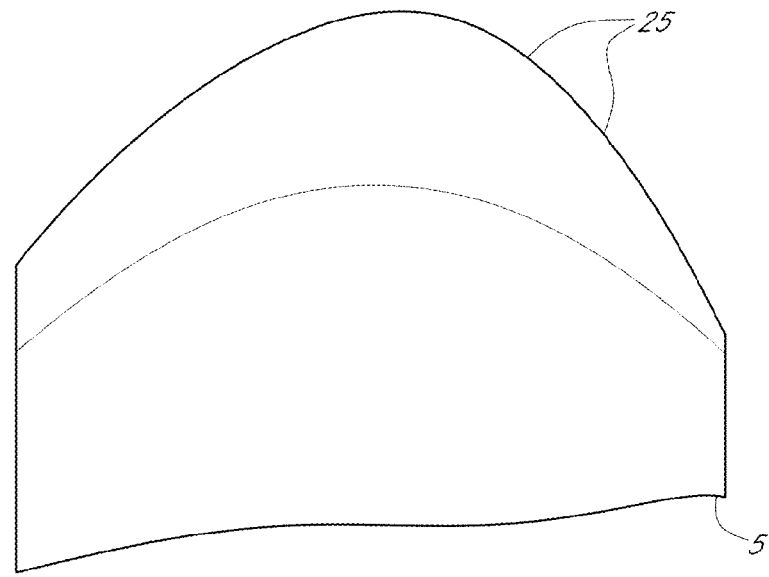
FIG. 9D is a side view of the single contiguous internal volume in a fully depressed position, where the inferior aspect has been actuated inferiorly modulating the volume into one large cavity, according to some embodiments.
Figure 10A:
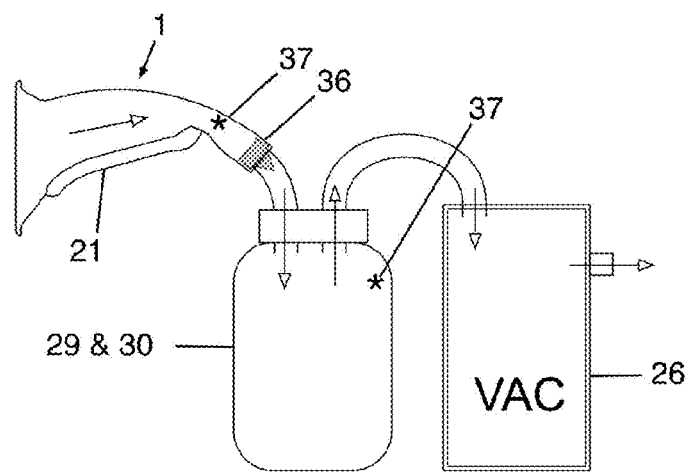
FIG. 10A is a schematic portraying the fluid expression device at rest while constant airflow is drawn through the structure by a vacuum resulting in a constant baseline negative pressure.
Figure 10B:
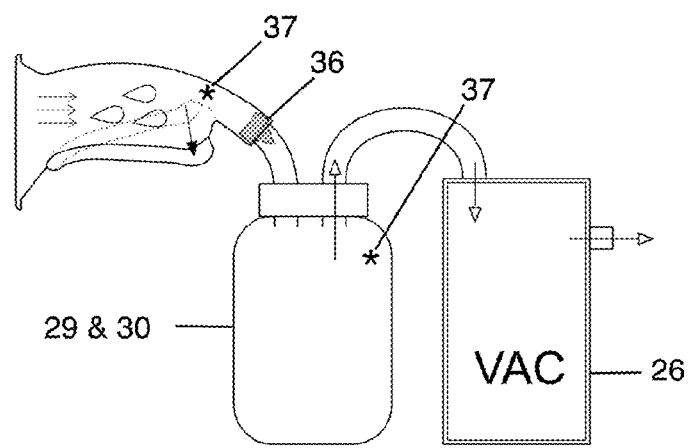
FIG. 10B is a schematic portraying the fluid expression device when the inferior aspect of the structure is depressed resulting in asymmetric volume modulation that decreases the negative pressure inside the internal volume. The volume modulation expresses fluid while the constant baseline negative pressure continues to be drawn by the vacuum.
Figure 10C:
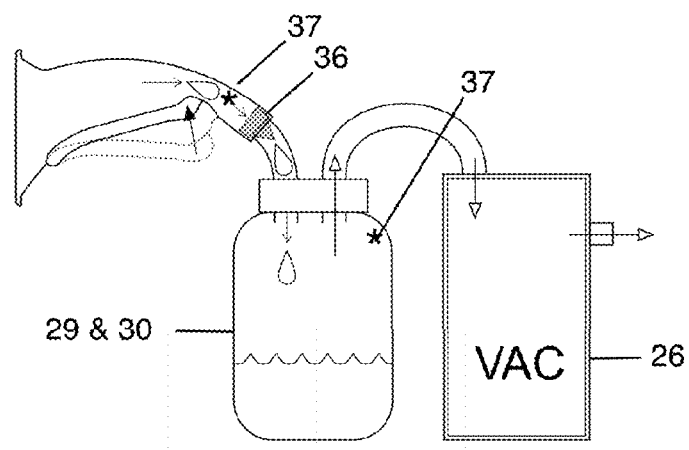
FIG. 10C is a schematic portraying the transport of expressed fluid from the structure into the receptacle as the inferior aspect of the structure is elevated to modulate the pressure differential within the internal volume. The internal volume pressure is returned to the constant negative baseline pressure upon elevation to the starting rest position.

FIGS. 9A-9D & 10A-10C detail the fluid expression as a result of the actuation of the inferior aspect 17 of the soft, contiguous structure 1. In some embodiments, the actuation can be accomplished by adhering to a ridge 14 cast along the inferior aspect 17 of the mold. In other cases, fixation can occur via any other bonding or adhering technologies obvious to one with skill in the art. In the rest position the actuation mechanism 34 can be fully elevated as in FIGS. 9A & 9B for example, resulting in the inferior aspect 17 of the oropharyngeal portion 4 coming into contact with the superior aspect, thereby separating the tube into two separate volumes 38 & 39. As the actuating mechanism 34 depresses shown in FIGS. 10A-10C, it can draw down the inferior aspect 17 of the oropharyngeal portion 4 with it, expanding the internal volume 25 of the oropharyngeal portion 4 into one large cavity as seen in FIGS. 9C & D, and drawing milk from the nursing mother's lactiferous ducts as shown in FIG. 10B. This mechanism is meant to mimic the tongue depression that generates fluid expression in a suckling infant. This actuation can be accomplished using micromotors of various types including, but not limited to, rotary motor actuation that is converted into linear actuation via gearing systems, screw drive systems, lever arm systems, or any other methodology known to one with skill in the art. Alternative possible motor actuation systems include, but are not limited to, servomotors, piston systems, slide rail systems, stepper motor systems, mini-track actuating motors, piezoelectric systems, electrostatic systems, magnetic systems, micro motors, and MEMS electrostatic actuation, MEMS stepper motor systems, MEMS piezoelectric actuation, or MEMS magnetic actuation Once a bolus of fluid has been expressed from the lactiferous ducts of the nursing mother, the asymmetric volume modification mechanism can elevate back to its starting position, in some embodiments creating, as shown in FIGS. 9A-9B two separate volumes 38 & 39 within the oropharyngeal portion 4, and pushing the bolus of fluid out the posterior of the oropharyngeal tube 5 into the waiting receptacle 29 & 30 as shown in FIG. 10C. In this way, each bolus of fluid can be evacuated from the internal volume 25 of the device at the end of each stroke cycle.

In some embodiments, the pressure within the internal volume 25 of the structure 1 returns to the negative baseline pressure, or slightly above, and does not return to ambient pressure until the expression session has been complete, and the device has been powered off or disengaged from the user. This application of direct, constant vacuum with a vacuum 26 to the internal volume 25 of the structure allows sub-atmospheric pressure to be achieved and maintained at the outset of the expression session and throughout the session. However, in some embodiments, the pressure within the internal volume 25 of the structure 1 does return to ambient prior to completion of the session.

Additional embodiments include a slight decrease (in other words, more negative pressure) in the vacuum baseline pressure (for example from −60 mm Hg to −80 mm Hg) during the fluid evacuation portion of each stroke cycle, depicted in FIG. 10C, to generate a pressure differential to encourage fluid evacuation from the internal volume 25 of the structure 1 into the waiting receptacle 29 & 30 at the end of each stroke.

Similarly, the actuation of the inferior aspect 17 can begin at a slightly lower elevation, such that upon returning to the elevated position, the inferior aspect 17 is elevated higher than the position in which it began. In this way, the additional elevation will increase the pressure slightly above the baseline pressure inside the internal volume 25 of the structure 1 (for example from −60 mm Hg to −50 mm Hg) such that fluid will be further encouraged to flow into the receptacle 29 & 30.

Alternatively, the use of an additional peristaltic actuation in the distal portion 5 of the single, contiguous structure 1 can also be employed to actively push the fluid through the structure 1 and into the waiting receptacle 29 & 30.

Also, an additional embodiment that involves no active transport of fluid, and relies entirely on gravity can exist in which the baseline pressure remains constant, and the starting and ending position of the actuation are the same.

A console 33 can be included in the device for the purposes of product design and housing of electronics, processing units, and batteries. Consoles 33 can be manufactured using any type of material including plastic, or malleable lightweight metal. The console 33 allows the housing of any batteries, electronics for micro-processing and controls, and pneumatics for generation of baseline pressure. The design allows for the use of any primary cell or secondary cell batteries, including but not limited to Alkaline batteries, Lithium-ion, Zinc-Carbon, or Nickel-iron, Nickel-cadmium, or Nickel metal hydride. The vacuum pumps 26 used can be, for example, either micro-vacuum pumps, including DC Brushless air-pumps, micro diaphragm air pumps, micro rotary diaphragm pumps, or MEMS designed pumps, allowing for, in some cases, low mass (~e.g., less than about 80 g), quiet mechanics (~e.g., less than about 50 dB), maximum pressure generated to be, e.g., less than about −160 mm Hg, and vacuum achievement degree to include, for example, the about −45 to −60 mm Hg range, but can extend beyond this range. Both the batteries and vacuum 26 pump systems can be housed within the console. Electronic circuit boards and microprocessors that can allow wireless connectivity and control of the device can also be housed within the console. In some cases, vacuum tubing can be included such that pneumatics can be transmitted from the vacuum pump head 26 to the oropharyngeal portion 4 of the soft, contiguous structure 1 via a port 5. Similarly, actuation motors or other actuation mechanisms 34 can be accommodated in custom designed positions within the console.

A variety of receptacles 29 & 30 can be used with systems and methods as disclosed herein to capture and store fluid. These can include, but are not limited to, glass bottles, plastic bottles, polyethylene bags, bags of different materials, larger plastic flexible canteens that can be worn around the lower torso of the user, glass vials, plastic vials, and rectangular glass and plastic storage receptacles. Each of these receptacles 29 & 30 can, in some cases, have a customized attachment to the distal opening 5 of the soft, contiguous structure 1 shown in FIG. 1-8 and/or the posterior aspect of the external rigid housing 2.

Figure 11:
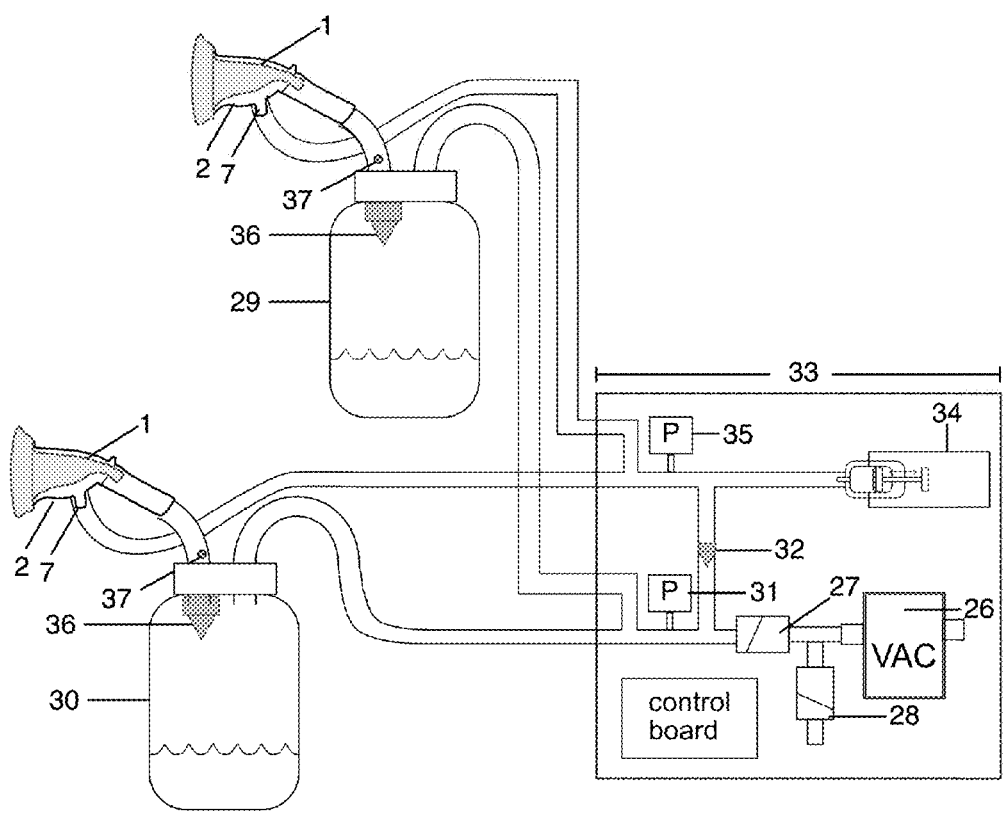
FIG. 11 is a schematic representation of one embodiment of the fluid expression device using a vacuum system to generate baseline pressure and an actuation mechanism to generate negative pressure inside the rigid external housing. The one-way valve between the rigid external housing and the receptacle has been moved downstream inside the receptacle.

FIG. 11 portrays an alternative embodiment where the one-way valve 36 between the soft, contiguous structure 1 and the receptacles 29 & 30 has been moved further downstream into the receptacles. The purpose of this configuration is to increase the volume impacted by the actuation mechanism 34.

Figure 12:
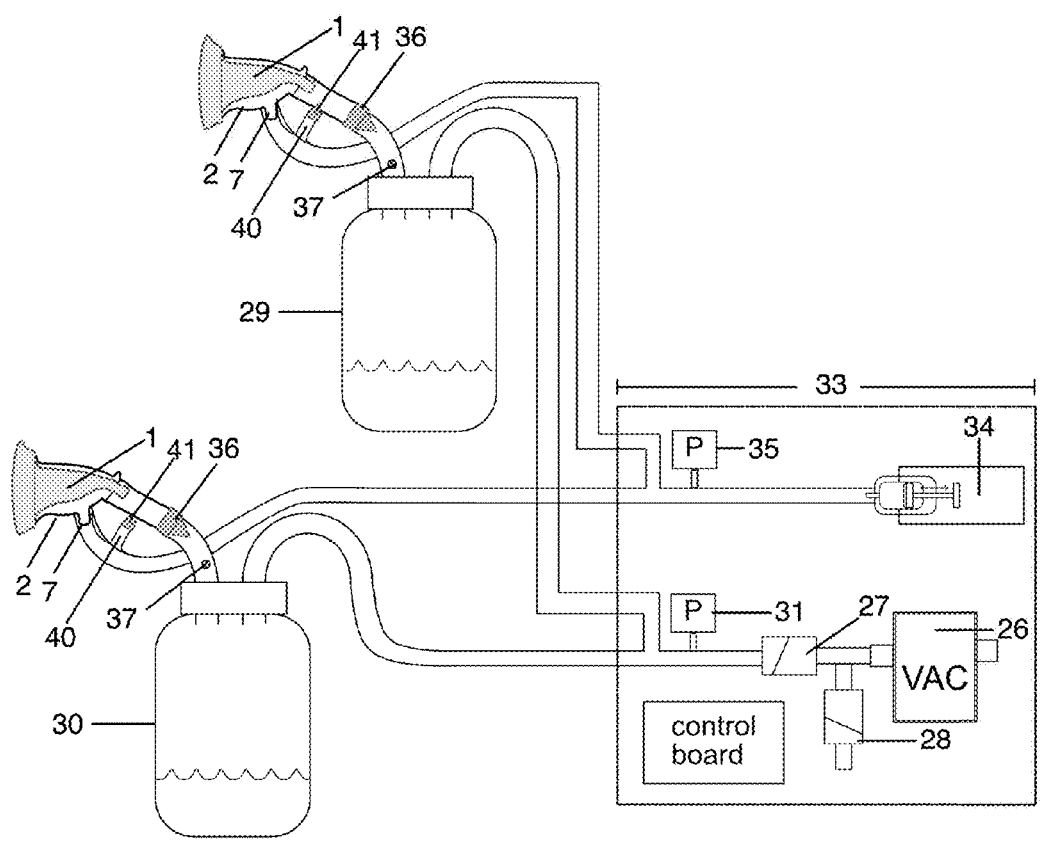
FIG. 12 is a schematic representation of one embodiment of the fluid expression device using a vacuum system to generate baseline pressure and an actuation mechanism to generate negative pressure inside the rigid external housing. An additional tube has been added to each side with a one-way valve oriented to allow air flow into the fluid line adding positive pressure with each return stroke of the actuating mechanism to assist fluid transport into the receptacle.

FIG. 12 portrays an alternative embodiment where an additional hose 40 has been added to each side of a bilateral system equipped with a one-way valve oriented to allow air flow to the fluid line in front of the one-way valve 41 between the soft, contiguous structure 1 and the receptacles 29 & 30. In this way, upon the return of the actuation mechanism 34 to its resting position, a positive pressure will be applied to the fluid line just proximal to the one-way valve 36 assisting milk transport into the receptacles 29 & 30.

Figure 13:
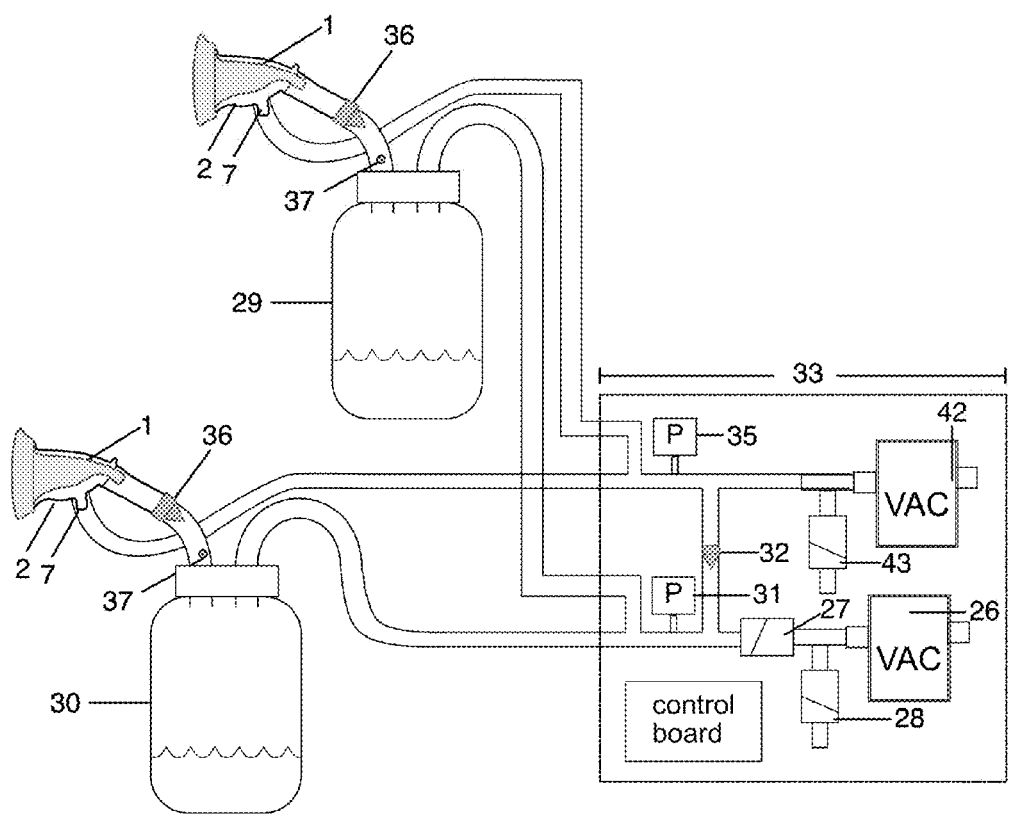
FIG. 13 is a schematic representation of one embodiment of the fluid expression device using a dual vacuum system using one vacuum system to generate baseline pressure and another to generate negative pressure inside the rigid external housing.

FIG. 13 portrays an alternative embodiment where the actuation mechanism has been replaced by a second vacuum 42 with an additional solenoid valve 43. In this embodiment, the actuation of the inferior aspect 17 of the soft, contiguous structure 1 is accomplished with a vacuum drawing between the baseline pressure (~−20 to −80 mm Hg) and the peak pressure (~−90 to −250 mm Hg). The return of the vacuum 42 to the baseline pressure on each stroke is controlled via a leak from the solenoid valve 43. In this way, a baseline pressure is still maintained, and the vacuum is able to operate at lower power and energy requirements than if it was controlling a full sweep from ambient pressure to peak pressure on each cycle.

Figure 14:
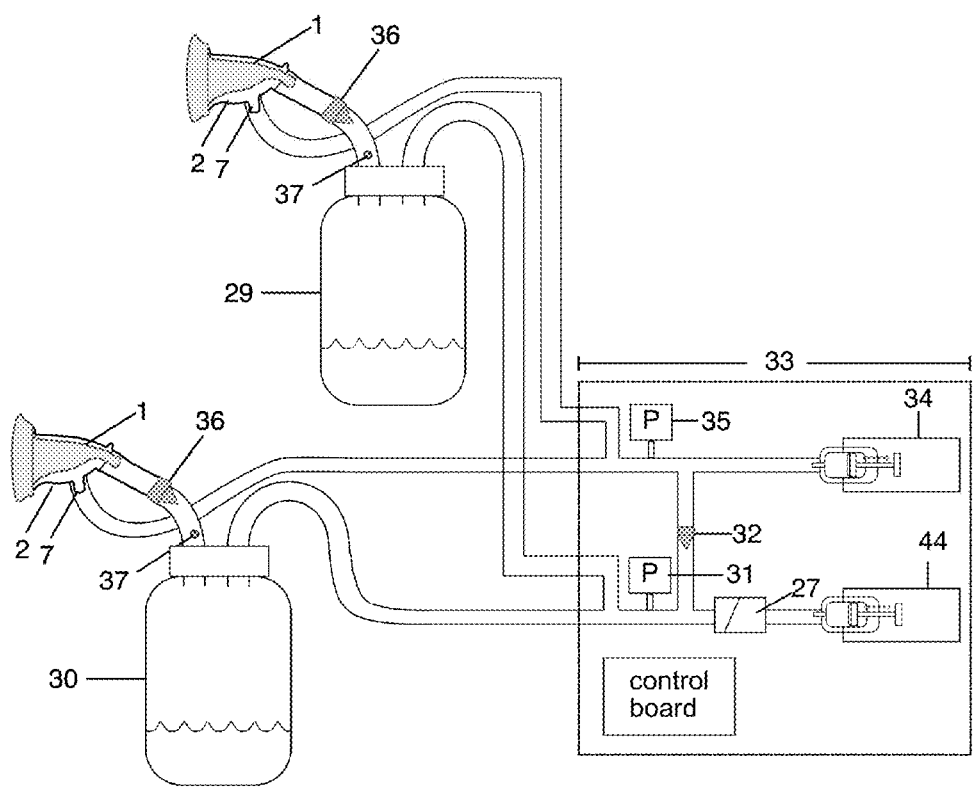
FIG. 14 is a schematic representation of one embodiment of the fluid expression device using a dual actuator system using one actuating mechanism to generate baseline pressure and another to generate negative pressure inside the rigid external housing.

FIG. 14 portrays an alternative embodiment where the baseline vacuum 26 has been replaced by a second actuation mechanism 44. In this embodiment, the second actuation mechanism 44 is drawn back until a desired baseline pressure is reached, as indicated by the inline pressure transducer 31. Once this baseline pressure is achieved, the actuation mechanism 44 is locked in place, in some cases using a solenoid locking mechanism 27, though other mechanisms known to one with skill in the art are possible, and the actuation mechanism 34 is triggered to begin the negative pressure fluid expression cycling as in previous embodiments. In this way, the system avoids the use of vacuums altogether, e.g., electrical vacuums. In the event that the baseline pressure is lost, the baseline pressure actuation mechanism 44, will return to its home position and oscillate between the home position and a small distance, in some cases between about 1-10 mm, until a significant increase, at least about 5 mm Hg, is read on the inline baseline pressure transducer 31. Upon reading the increase in pressure, the baseline actuation mechanism 44 will again draw back until the desired baseline pressure is reached, as read by the baseline pressure transducer 31, and the negative pressure cycling actuation mechanism 34 can resume.

Figure 15:
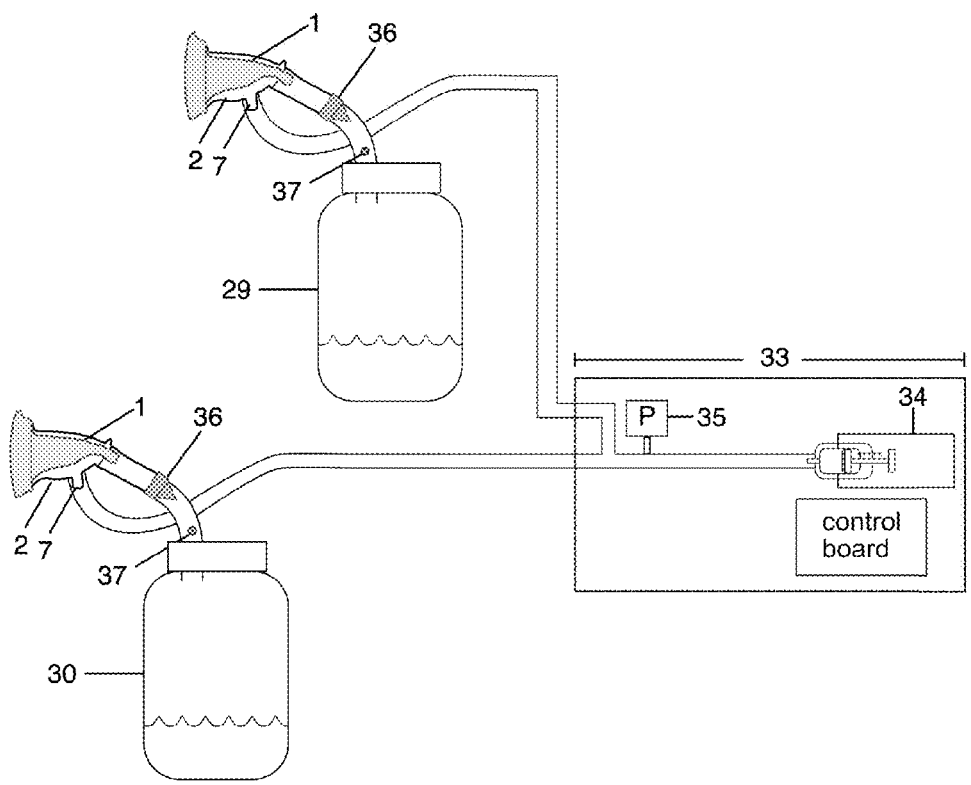
FIG. 15 is a schematic representation of one embodiment of the fluid expression device using a single actuator system to generate both baseline pressure and to generate negative pressure inside the rigid external housing. This same system can be used to drive the biomimetic structure without a baseline if so desired.

FIG. 15 portrays an alternative embodiment that uses just one actuation mechanism 34 to achieve baseline vacuum and to operate the negative pressure fluid expression cycling. In this embodiment, the single actuation mechanism 34 draws negative pressure until the desired baseline vacuum is reached. Upon reaching the desired baseline vacuum pressure, as indicated by the pressure transducer 31, the actuation mechanism 34 begins the negative pressure fluid expression cycling from the new rest position and the peak pressure position as prescribed by the user. In the event that the baseline pressure is lost, the actuation mechanism 34, will return to its home position and oscillate between the home position and a small distance, in some cases between about 1-about 10 mm, until a significant increase, at least about 5 mm Hg, is read on the pressure transducer 31. Upon reading the increase in pressure, the actuation mechanism 34 will again draw back until the desired baseline pressure is reached, as read by the pressure transducer 31, and the negative pressure cycling actuation mechanism 34 can resume.

An alternative embodiment using the architecture shown in FIG. 15 involves a system where the baseline vacuum pressure is not included. In this embodiment, the actuation of the inferior aspect 17 of the soft, contiguous structure 1 is accomplished via an actuation mechanism 34 to achieve pressure gradations from ambient pressure to peak pressure. In this embodiment, the asymmetrical actuation of the soft, contiguous structure 1 is accomplished on the downstroke of the actuation mechanism 34, and the asymmetrical collapse, if any, is exhibited on the upstroke of the actuation mechanism 34. In this way, the system can be used to apply a massaging or tactile effect to the nipple-areola complex without constricting the anatomy in a significant way.

Figure 16:
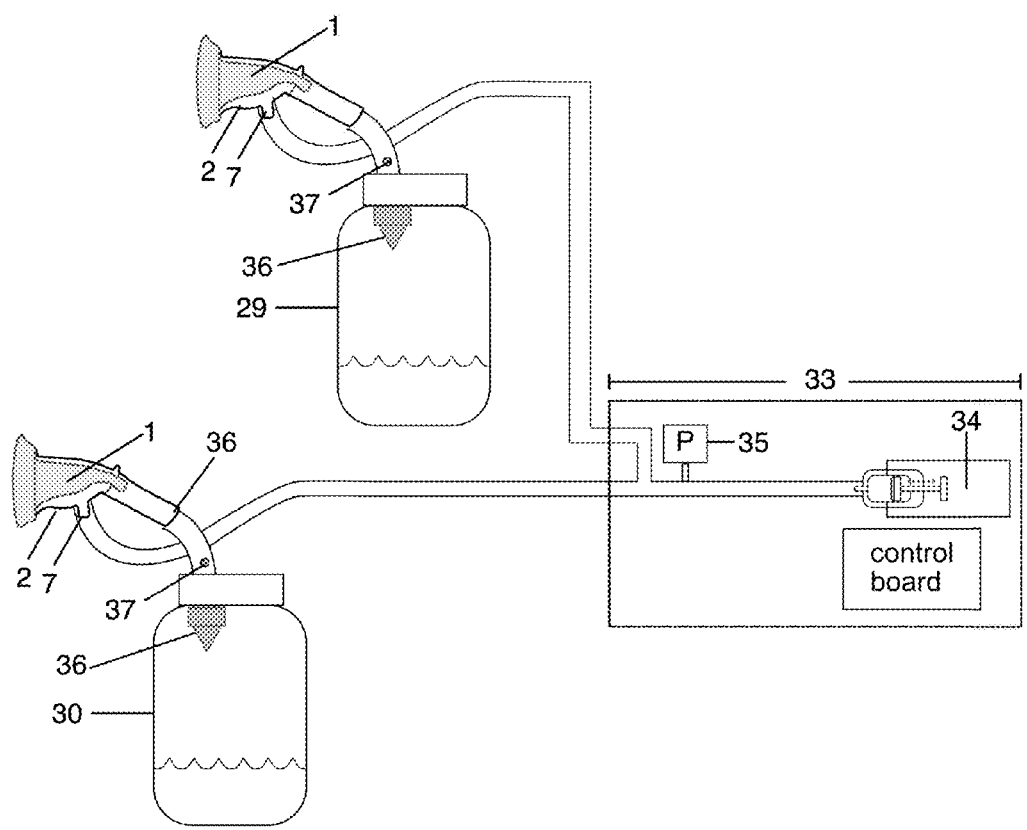
FIG. 16 is a schematic representation of the single contiguous structure with an actuation mechanism adhered to the longitudinal ridge, according to some embodiments of the invention.

FIG. 16 shows an alternative embodiment of a system that discards the baseline vacuum, but includes the asymmetrical actuation of the soft contiguous structure 1 via an actuation mechanism 34. In the present embodiment, the duckbill valve 36 has been moved into the receptacles 29 & 30 to allow a larger working volume during the actuation. Again, the asymmetrical actuation of the soft, contiguous structure 1 is accomplished on the downstroke of the actuation mechanism 34, and the asymmetrical collapse, if any, is exhibited on the upstroke of the actuation mechanism 34. In this way, the system can be used to apply a tactile effect to the nipple-areola complex without constricting the anatomy in a significant way.

Figure 17:
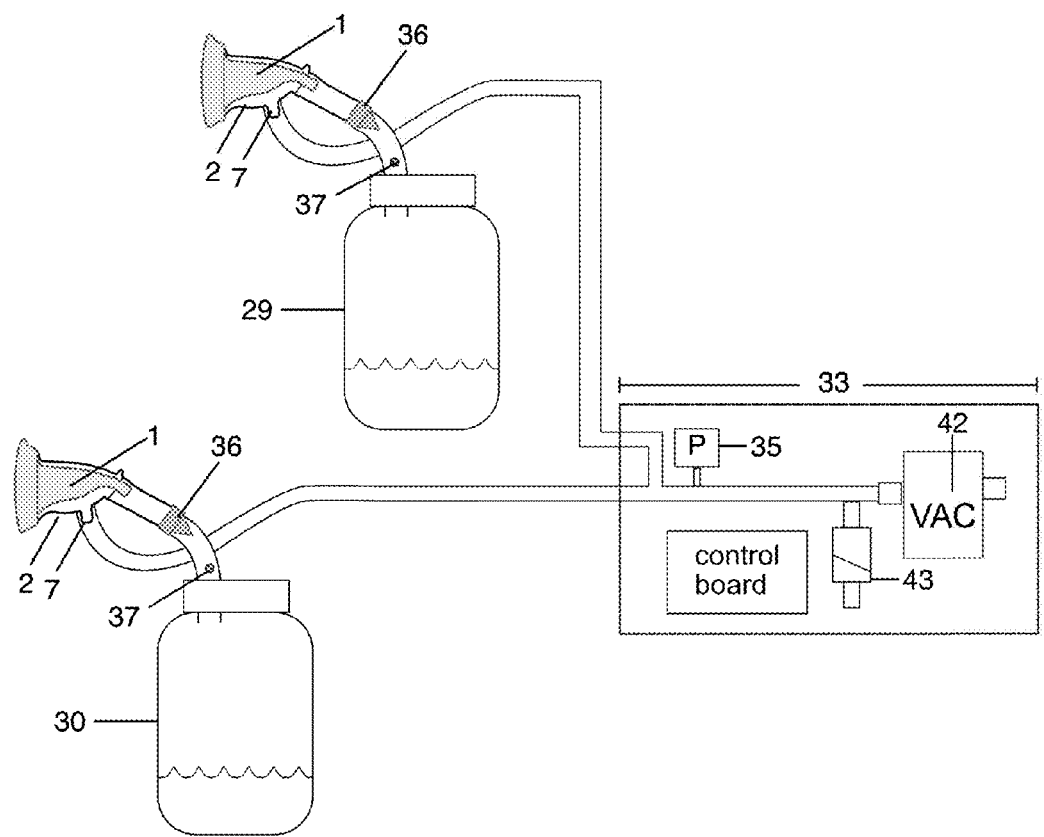
FIG. 17 shows an embodiment in which the actuation mechanism has been replaced with a vacuum to accomplish the actuation of the inferior aspect of the soft, contiguous structure.

FIG. 17 shows a similar embodiment in which the actuation mechanism 34 has been replaced with a vacuum 42 to accomplish the actuation of the inferior aspect 17 of the soft, contiguous structure 1. The vacuum is able to draw a negative pressure until the desired peak pressure, as read on the pressure transducer 35. Once the desired peak pressure has been reached, the solenoid valve 43 is used to leak the air pressure back to the desired level.

Figure 18:
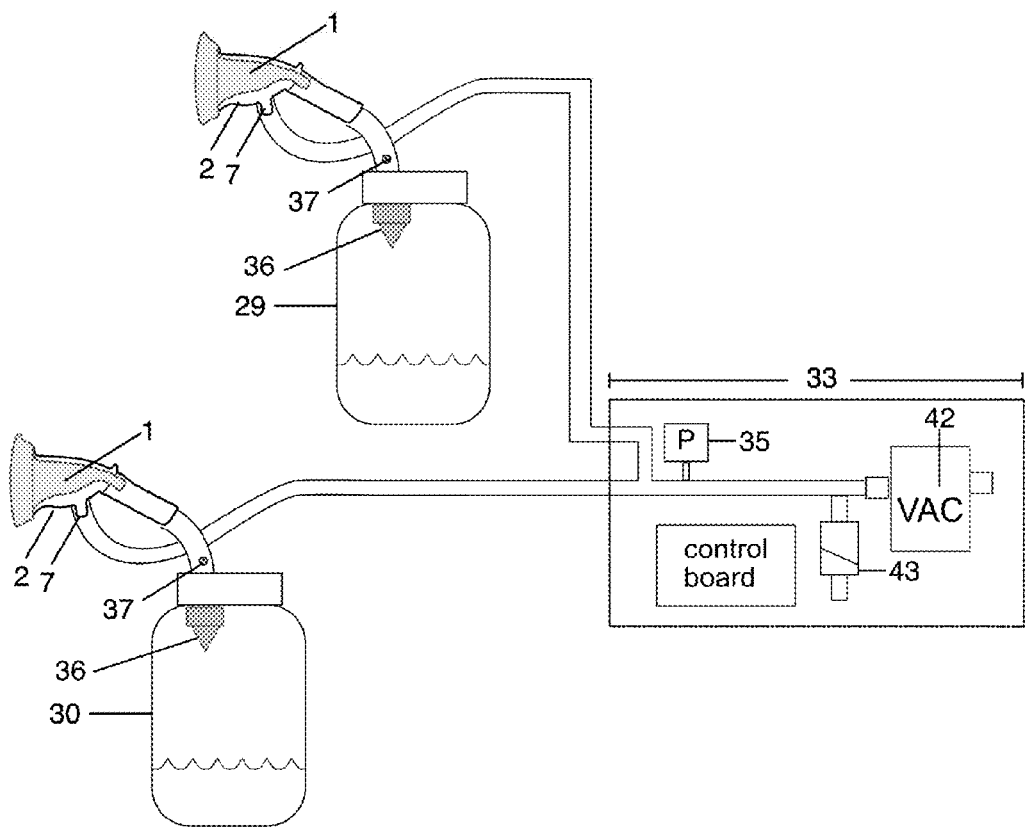
FIG. 18 shows an alternative embodiment of a system that does not include a baseline vacuum, but includes the asymmetrical actuation of the soft contiguous structure via a vacuum.

FIG. 18 shows an alternative embodiment of a system that does not include the baseline vacuum, but includes the asymmetrical actuation of the soft contiguous structure 1 via a vacuum 42. In the present embodiment, the duckbill valve 36 has been moved into the receptacles 29 & 30 to allow a larger working volume during the actuation. Again, the asymmetrical actuation of the soft, contiguous structure 1 by the draw of the vacuum 42, and the return of the negative pressure to the desired resting pressure is achieved via the solenoid valve 43 leak.

The embodiments described herein can all be applied to mammals of different species, altering the anatomy and biomechanics to accommodate the differences in scale, anatomy, and physiology. For example, in dairy calves, the lengths of the oropharyngeal space, major and minor axes of the proximal opening, thickness of the liner, and the actuation length of the liner can all be increased to match the anatomical values found in the academic literature. Specifically, these values can accommodate, in some embodiments, average teat lengths of 56-66 mm, teat diameters of 26-30 mm, teat wall thicknesses of 7-8 mm, and teat canal lengths of up 11 mm. Baseline pressures can be modified to accommodate those seen in nursing calves ranging from 55 mmm Hg to 130 mm Hg. These changes can allow the same mechanism of all embodiments defined herein to be used to generate pressures closer to 500 mm Hg, which approximate those reached in a nursing calf. The asymmetric collapse and actuation of the flexible liner can be maintained such that radial collapse around the teat end cannot occur as seen in the majority of dairy liners on the market today. This mechanism can allow the optimization of fluid flow through the lactiferous ducts and emptying the udder more efficiently and completely in each milking session. The cycle frequency can be increased to 2 Hz to match those seen in nursing calves to ensure optimal pressure waveforms for efficient and comfortable milk expression.

Figure 19:
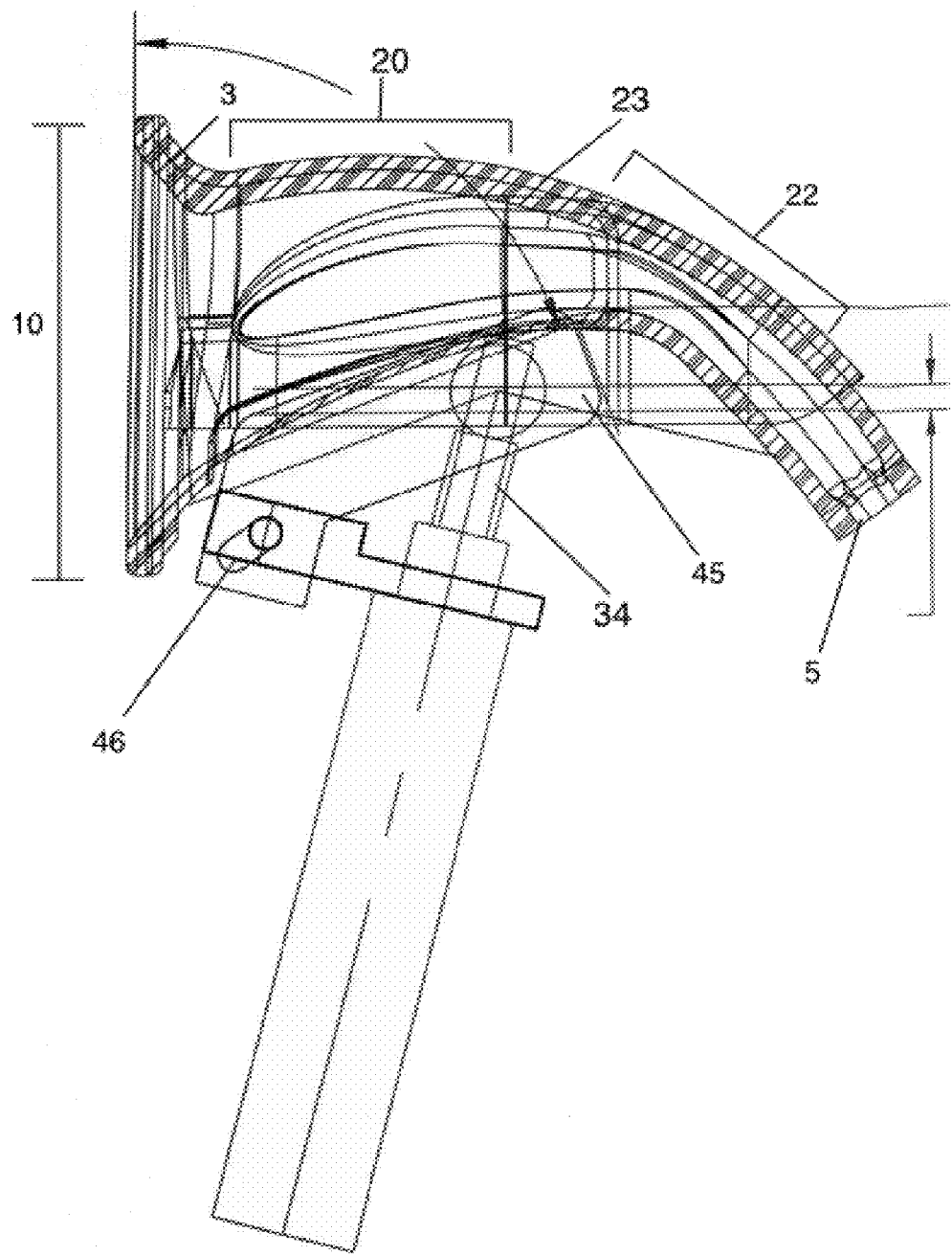
FIG. 19 shows an alternative embodiment of a system that allows for a smaller anterior actuation along with the larger posterior actuation using an actuation platform.

In some embodiments, the allowance of a smaller anterior actuation along with the larger posterior actuation can be accomplished using an actuation platform 45 as portrayed in FIG. 19. The primary actuation occurs at the axial position of the hard-soft palate junction 23 via the actuation mechanism 34 on the inferior aspect 17 of the oropharyngeal portion 4, while a slotted trackway 46 allows limited movement of the anterior portion of the soft structure 1. This slotted trackway 46 can be modulated to allow greater or lesser excursions as is deemed necessary. Additional embodiments can include an actuation platform shaped in such a way that a trackway is unnecessary for small anterior excursions to occur.

Some embodiments of the actuation system can replicate the traveling wave of tongue elevation starting at the tip of the tongue using just one actuation positioned at the junction of the hard and soft palate 23 on the inferior aspect of the oropharyngeal cavity 17. The density of the inferior aspect 17 of the oropharyngeal portion 4 can vary along its length such that an actuation at one point results in variable movements along the length of the soft structure based on the material properties of the structure and the movement of the single actuator 34.

Some embodiments of the actuation system can replicate the traveling wave of the tongue elevation starting at the tip of the tongue using multiple sequentially activated actuation mechanisms, each elevating and depressing portions of the inferior aspect 17 of the oropharyngeal portion 4 of the structure 1 independently of one another and to variable magnitudes. In these embodiments, the inferior aspect 17 of the oropharyngeal portion 4 can either be consistent along its length or it can vary. The multiple actuation mechanisms can elevate and depress in a traveling fashion from anterior to posterior to generate a traveling wave of tongue elevation and depression. The most anterior motor can begin depression prior to the completion of elevation of the most posterior motor, such that each wave overlaps with the prior wave, similar to what has been reported in the biomechanical literature.

Some embodiments of the wave-like actuation pattern can be achieved using a trackway lying directly beneath the inferior aspect 17 of the oropharyngeal portion 4, and oriented longitudinally along its length. This trackway would be oriented with its posterior end at an elevated position, allowing the movement of a pin along its length, and back again to simulate the rolling peristaltic elevation and depression of the tongue.

Some embodiments of the actuating mechanism can take advantage of the mechanical properties of the soft, flexible material used to mimic the oropharynx of the infant. In some embodiments, the actuator 34 may only be active in the tongue depression portion of the cycle, acting like a spring that depresses the inferior aspect 17 of the oropharyngeal portion 4 of the structure 1 actively, and passively recoils to the elevated position. Thus, the spring is slowly loaded via an actuation mechanism 34 of any of the previously described types, and then released for the tongue elevation portion of the cycle. The timing of tongue elevations can be calibrated via the spring constant of the mechanism, and the passive mechanical properties of both the recoil of the spring, as well as the recoil of the soft material of the oropharyngeal portion of the structure 1, can serve to develop the positive pressure to return the tongue to its baseline position.

In some manual embodiments of the device, the biomimetic soft structure 1 can remain the same, however, the console and the associated battery, onboard microprocessor and electronics, and vacuum 26 can be excluded. In some embodiments, the user can create the baseline pressure by drawing out a piston from the posterior end 5 of the soft structure 1, and locking the piston in place. The length of the piston, and the resistance can be set to generate approximately −45 to −80 mm Hg of baseline pressure. Once the baseline pressure has been locked into place, a rotary crank shaft can be rotated by the user, and a gearing cam shaft can translate that rotary motion into elevation and depression of the linear actuation mechanism 34. Other mechanisms of manual actuation of the inferior aspect of the liner can also be employed including lever arm systems, diaphragm systems, bellows structures, and any other manual actuation mechanism known to one with skill in the art. In this scenario, cycle frequency and duty cycle can be set by the user's own rhythm of cranking. No electronics are necessarily required, and the system can be an exclusively manual pumping system without any electronics or motorized components in some embodiments.

For electronic systems, user control can be achieved with an onboard analog dial, one or more buttons, a touchscreen, or other user interface for cycle frequency and pressure settings. In some embodiments, the duty cycle can be modulated automatically via the microprocessor based on the cycle frequency chosen by the user. In some embodiments of the device, the user can toggle between nutritive and non-nutritive suckling using a switch or button on the device.

In some embodiments, systems and components as described herein can take the form of a computing system that is in communication with one or more computing systems and/or one or more data sources via one or more networks. The computing system may be used to implement one or more of the systems and methods described herein. While various embodiments illustrating computing systems and components are described herein, it is recognized that the functionality provided for in the components and modules (which may also be referred to herein as engines) of computing system may be combined into fewer components and modules or further separated into additional components and modules. For example, a communications engine may include a first module in communication with a diagnostic imaging modality and a second module in communication with a destination modality. Modules can include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Any modules can be executed by one or more CPUs.

A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein can be implemented as software modules, but may be also represented in hardware or firmware. Generally, the modules described herein refer to logical modules that may be combined with other modules or divided into sub-modules despite their physical organization or storage. In addition, all the methods described herein may be executed as instructions on a CPU, and may result in the manipulation or transformation of data.

In some embodiments, hardware components of the system includes a CPU, which may include one, two, or more conventional microprocessors. The system further includes a memory, such as random access memory ("RAM") for temporary storage of information and a read only memory ("ROM") for permanent storage of information, and a mass storage device, such as a hard drive, flash drive, diskette, or optical media storage device. Typically, the modules of the system are connected using a standard based bus system. In different embodiments, the standard based bus system could be Peripheral Component Interconnect ("PCI"), Microchannel, Small Computer System Interface ("SCSI"), Industrial Standard Architecture ("ISA") and Extended ISA ("EISA") architectures, for example.

In accordance with some embodiments, systems can be operatively coupled to a destination modality, such as, for example, a software program on a desktop computer, or mobile device such as a laptop, smartphone, or tablet for example, or an electronic medical record ("EMR") in some embodiments. EMRs may be any software or hardware-software system configured to store and provide access to electronic medical data. In accordance with various embodiments, EMRs may be at least one of an electronic medical record, an electronic health record, and the like. In some embodiments, systems and components thereof can be operatively coupled to a destination modality that can be an email or other messaging modality; SAMBA, Windows, or other file sharing modality; FTP or SFTP server modality; a VPN; a printer; and the like.

In accordance with some embodiments a system may comprise one, two, or more software modules, a logic engine, numerous databases and computer networks configured to provide a user with access to various modalities as described herein. Systems may be configured such that patient data, or no patient data is recorded by the system. While the system may contemplate upgrades or reconfigurations of existing processing systems, changes to existing databases and business information system tools are not necessarily required. Systems may be implemented or integrated into existing healthcare information management systems, such as EMRs, without changes to the EMR system, and may interface with other modalities without changes to the communication system of the modality.

In accordance with some embodiments, systems may be software or hardware-software systems. For example, systems can include a communication engine configured to receive and transmit information operatively coupled to an information converter configured to render information in a suitable format for storage; a work list engine configured to create a user selectable task list from orders and selectable by a user; and an event log configured with a user selectable record of transactions and/or errors in data transmission and/or data conversion performed by the system.

In accordance with some embodiments, communication engine may be any software or hardware software-system configured to receive and/or transmit data. Communication engine may be configured to transmit and receive data over a variety of network interfaces including wired and wireless networks or a combination thereof, such as via Ethernet, 802.11x, Bluetooth, FireWire, GSM, CDMA, LTE, and the like. Communication engine may also be configured to transmit and/or receive data with file transfer protocols such as TCP/IP, as well as various encryption protocols, such as, for example, WEP, WPA, WPA2, and/or the like.

Figure 20A:
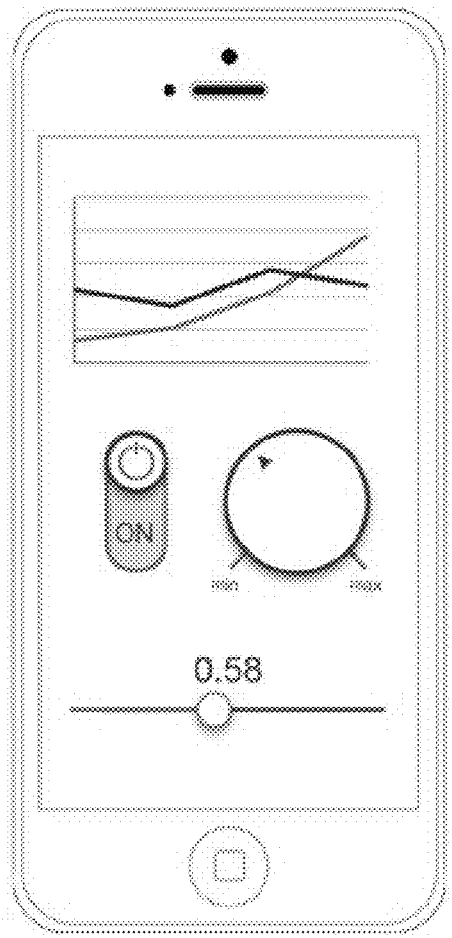
FIG. 20A is a representation of a control screen for a smartphone or tablet application including, but not limited to, cycle control and frequency, power, and graphing capabilities, according to some embodiments.
Figure 20B:
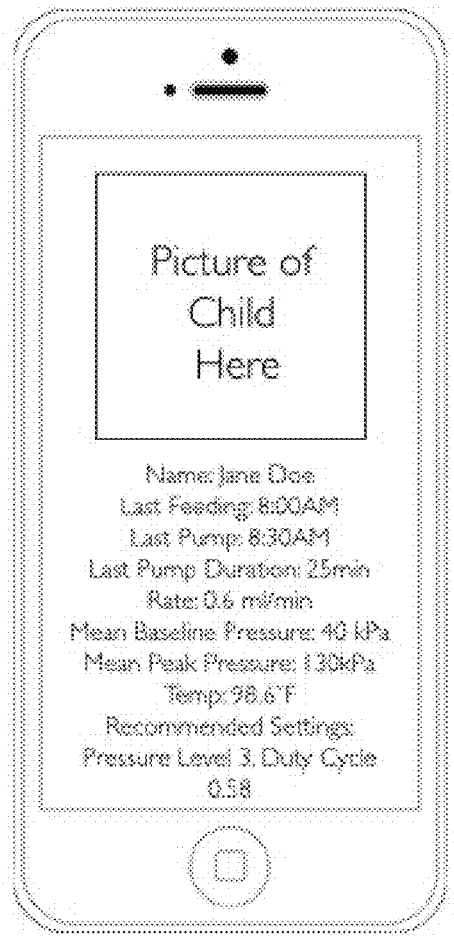
FIG. 20B is a representation of an additional data screen for a smartphone or tablet application including, but not limited to, infant identification information, last recorded feeding, last recorded pumping, last recorded pump time, rate of fluid expression, mean baseline pressure, mean peak pressure, fluid temperature, and recommended settings for next pump, according to some embodiments.

Some embodiments of the device include user control via a remote device such as a smartphone or tablet device as shown in FIGS. 20A-20B. This wireless connectivity can be enabled by, but not limited to, infrared wireless communication, radio frequency wireless communication (including, but not limited to Bluetooth communication), microwave wireless transmission, Wi-Fi networking, or satellite communications. Using any of these wireless communications, the user's tablet or smartphone can be able to control one or more of: tongue depression and elevation magnitudes, toggle between nutritive and non-nutritive suckling cycles, duty cycle can be modulated or set automatically by the microprocessor algorithm, and cycle frequency can be modulated. The control system can be accessible through a customized application interface that will sync across devices.

In smartphone and tablet embodiments, the device can also sync with a desktop computer, laptop computer, or web based application to upload user data. User data can then be analyzed by custom software algorithms to deliver analytic results for the personal user, and, if the user allows, comparison to data gathered from additional users to compare pumping variables. In addition, smartphone and tablet applications can allow for the uploading of personal data, including media such as, for example, photographs and videos of the nursing infant for the breastfeeding mother to view during pumping sessions.

FIG. 20A is a representation of a control screen for a smartphone or tablet application including, but not limited to, cycle control and frequency, power, and graphing capabilities, according to some embodiments.

FIG. 20B is a representation of an additional data screen for a smartphone or tablet application including, but not limited to, infant identification information, last recorded feeding, last recorded pumping, last recorded pump time, rate of fluid expression, mean baseline pressure, mean peak pressure, fluid temperature, and recommended settings for next pump, according to some embodiments.

Variables to be monitored and analyzed can be collected with micro sensors 36, or MEMS based sensors, that can be implanted within the soft structure 1, within the external rigid housing 2, or within the receptacles 29 & 30. These environmental sensors 37 can include, but are not limited to (non-limiting examples listed in parentheticals to follow), mechanical sensors (force, pressure, velocity, acceleration, position), thermal sensors (temperature, entropy, heat, and heat flux), magnetic sensors (field intensity, flux density, magnetic moments, permeability), chemical sensors (chemical concentration, chemical composition, reaction rate), electromagnetic sensors (radiant, EM wave intensity, phase, wavelength, polarization, reflectance, refractive index, transmittance), electro-optical sensors (through-beam, reflective, diffuse, position sensors, IR sensors), and electrical sensors (voltage, current, charge, resistance, capacitance, polarization). These sensors 37 can be used to deliver variables such as last feeding times, last pumping times, rate of fluid expression, mean baseline pressure, mean peak pressure, temperature of milk, and many other variables as shown in FIG. 20B. Based on the analysis of these variables, the algorithms can recommend optimal cycle frequencies and duty cycles for each user specific to their personal milk production.

More specifically, in some embodiments, environmental sensors 37 can be used to automate device settings to optimize fluid expression, and to deliver information to the user regarding fluid expression biomechanics, health, and function. An algorithm that takes the input voltage from a pressure sensor and flow sensor can be used to evaluate the pressure waveform. In an initial profiling period of device use, the signals can be initially filtered and synced to one another, and evaluated to determine the fluid flow at specific pressure and cycle settings. A general threshold of mean peak pressures can be selected, e.g., from the academic literature and can be used to modulate the pressure setting for a specific user to determine peak fluid flow during initial uses for both non-nutritive and nutritive sucking cycles. After each use of the device, the system can report the mean peak pressures for each phase of the session, the timing to the let-down reflex, the number of secondary or tertiary let-down reflexes, the expressed fluid volume during each nutritive cycle, and/or the flow rate for each nutritive cycle. Based on one, two, or more of these variables, the device can recommend pressure settings for each non-nutritive and nutritive sucking cycle for future uses. Over time, the algorithm can settle on an optimized pressure setting for each cycle customized for each specific user. This system-analyzed optimal setting can be modifiable by user input, and user-modified settings can be compared to system-analyzed optimal settings to allow the user to modify pressures based on discomfort or personal preference. In this way, the algorithms can be able to optimize pressure settings for non-nutritive sucking cycles that yield the most rapid transitions to nutritive sucking cycles, and pressure settings for nutritive sucking cycles that yield the greatest fluid volume expressed.

In addition, pressure and fluid sensation can allow the profiling of the let-down reflex (transition from non-nutritive to nutritive sucking) allowing the system to automatically transition from non-nutritive cycle parameters to nutritive cycle parameters. In this way, the transition to the slower non-nutritive cycle can be automated and customized to each individual user. Similarly, the system can be able to detect any transitions from nutritive cycling back to non-nutritive, and will resume a non-nutritive cycle based on settings and cycle frequencies that it has previously optimized during the aforementioned profiling phase of device use.

Some embodiments of the device can include one, two, or more chemical sensors to detect fat, glucose, protein, or other nutrition content in fluid expressed. The inclusion of a chemical sensor to allow quantification of lipid or other content in each sample volume of fluid can offer the user information regarding the expression of hind milk content. This sensor 37 can be incorporated into the soft structure 1 itself or into receptacles 29 & 30 used to retain fluid that the device has expressed. If included within the structure 1 itself, the sensor could be a MEMS-based microfluidic sensor that allows real-time lipid content quantification with each sample of fluid expressed.

In some embodiments, the device can capture maternal heart rate, blood pressure, respiratory rate, or other physiologic parameters during the various cycles of each session to provide information regarding how heart rate or other physiologic parameters impacts milk yield.

In some embodiments, the system can offer total milk volume projections and number of session requirements based on user input. User inputs of estimated milk volume needs per day can be used as an input, and combined with mean fluid volume per session, and cross-referenced against the fluid volume and time between sessions, to project additional pumping sessions throughout the day to achieve desired goals. Further, the system can log time of day for each pumping session, session length, energy/battery power usage per session, cycles per minute throughout each session and during each cycle within a session, number of let-down events during each session, milk volume expressed throughout each session, rate of expression throughout each session, and duration of pumping sessions. Any of the data outputs disclosed herein can be shown on a display on the device itself, a smartphone, tablet, computer, or other element.

In addition to the environmental sensors 37, a heating mechanism can be included within the rigid external housing 2 to offer temperature modulation for the single, contiguous structure 1. This heating of the structure within the device is intended to mimic the warmth of the infant's oral cavity and to physiologically stimulate the nursing mother.

Various other modifications, adaptations, and alternative designs are of course possible in light of the above teachings. Therefore, it should be understood at this time that the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described. Any methods disclosed herein need not be performed in the order recited. The methods disclosed herein include certain actions taken by a practitioner; however, they can also include any third-party instruction of those actions, either expressly or by implication. For example, actions such as "expressing fluid from a breast" includes "instructing the expressing of fluid from a breast." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A mammalian fluid expression device comprising:
a soft, contiguous, partially collapsible structure comprising a fixed superior aspect, a movable inferior aspect, and an internal channel therethrough that can receive a nipple-areola complex when in use, and connect to a receptacle,
wherein when actuated for fluid expression, the inferior aspect of the soft structure is configured to be repeatedly asymmetrically deformed in an inferior direction away from the fixed superior aspect to generate negative pressure gradients within the internal channel and express fluid, and wherein upon fluid expression, fluid is transported inferiorly from the soft structure into the receptacle.

2. The fluid expression device of claim 1, wherein the device includes a manually engaged piston calibrated to set a baseline pressure, and a rotary shaft or lever arm to allow manual actuation of the inferior aspect of the structure resulting in the negative pressure gradients within the internal channel for fluid expression.

3. The fluid expression device of claim 1, wherein at least one environmental sensor is included within the structure, within the housing, and/or within the receptacle to allow the capturing of environmental data.

4. The fluid expression device of claim 3, further comprising a controller configured to process and quantify the data and make the data available for user and researcher data collection and analysis, as well as used to automate pump settings specific to individual users, and optimize fluid expression and minimize discomfort.

5. The fluid expression device of claim 1, wherein the device is configured to automatically transition between a stimulative and non-stimulative cycle multiple times throughout a fluid expression session.

6. A mammalian fluid expression device comprising:
a single, contiguous, partially collapsible structure comprising a biocompatible, flexible material configured to receive a nipple-areola complex when in use, the structure including: an internal volume, a proximal end with an elliptical profile configured to receive a nipple-areola complex when in use for fluid expression; and
an external rigid fixed housing configured to mimic an infant's oropharyngeal cavity, wherein the housing includes stiffening elements configured to replicate the bony anatomy and the form of the inferior aspect of an oropharyngeal cavity during peak negative pressure while breastfeeding,
wherein the housing is configured to receive the single, contiguous structure within the housing,
wherein a distal end of the structure has a smaller diameter than the proximal end of the structure, and the distal end of the structure is configured to connect to a receptacle or vacuum source such that fluid flows in an inferior direction into the receptacle or vacuum source,
wherein the device is configured to be connected to a continuous vacuum to generate constant baseline sub-atmospheric pressure, resulting in a primed system state,
wherein asymmetric volume deformation via cyclic depression of an inferior aspect of the structure in an inferior direction away from a fixed superior, stiffer aspect of the structure and away from the nipple-areola complex when the device is attached to a portion of a breast creates an interior volume modulation of the single contiguous structure resulting in negative pressure gradients within the internal volume for fluid expression.

7. The fluid expression device of claim 6, wherein the structure comprises an oropharyngeal portion comprising variable thicknesses circumferentially such that the thickness of the material increases gradually from the inferior aspect up along the lateral aspect and towards the superior aspect of the structure; and the superior portion mimics the hard and soft palates of the infant, wherein an anterior portion is the thickest, most stiff portion of the structure, and a posterior portion is thinner than the anterior portion.

8. The fluid expression device of claim 6, wherein upon generation of constant baseline sub-atmospheric pressure, the variation in stiffness of the structure allows for asymmetrical collapse along the length of the inferior aspect of the structure against the superior, stiffer, portion of the structure while accommodating the received nipple-areola complex.

9. The fluid expression device of claim 6, wherein the device includes a manually engaged piston calibrated to set the baseline pressure, and a rotary shaft or lever arm to allow manual actuation of the inferior aspect of the structure resulting in negative pressure gradients within the internal volume for fluid expression.

10. The fluid expression device of claim 6, wherein at least one environmental sensor is included within the structure, within the housing, and/or within the receptacle to allow the capturing of environmental data.

11. The fluid expression device of claim 10, further comprising a controller configured to process and quantify the data and make the data available for user and researcher data collection and analysis, as well as used to automate pump settings specific to individual users, and optimize fluid expression and minimize discomfort.

12. The fluid expression device of claim 6, wherein the pumping cycle automatically transitions between a stimulative and non-stimulative cycle multiple times throughout a pumping session.

13. The fluid expression device of claim 6, wherein the device is configured to be controlled using a web/mobile user interface accessible from a user's smartphone, tablet or another remotely connectable device.

14. A mammalian fluid expression device comprising:
a single, contiguous, partially collapsible structure having an internal cavity, a proximal end and a distal end and comprising a biocompatible, flexible material configured to receive a nipple-areola complex, the proximal end comprising an elliptical profile configured to receive a nipple-areola complex when the device is in operation, the structure further including a movable inferior aspect and a fixed superior aspect, wherein the fixed superior aspect has a stiffness that is greater than that of the inferior aspect; and a rigid housing configured to house the soft, contiguous structure therein, wherein the distal end of the structure has a smaller diameter than the proximal end, and wherein the distal end is capable of connecting to a receptacle or vacuum source such that fluid expressed flows into the receptacle or vacuum source in an inferior direction, wherein asymmetric volume deformation via cyclic depression of the movable inferior aspect of the structure in an inferior direction away from the fixed superior, stiffer, aspect of the structure and away from the nipple-areola complex when the device is in operation and interfaces with a portion of a breast creates an interior volume modulation of the single contiguous structure resulting in negative pressure gradients within the internal cavity for fluid expression.

15. The fluid expression device of claim 14, wherein the structure comprises an oropharyngeal portion comprising variable thicknesses circumferentially such that the thickness of the material increases gradually from the inferior aspect up along a lateral aspect and towards the superior aspect of the structure, wherein an anterior portion is the thickest, most stiff portion of the structure, and a posterior portion is thinner than the anterior portion.

16. The fluid expression device of claim 14, wherein the device includes a manually engaged piston calibrated to set the baseline pressure, and a rotary shaft or lever arm to allow manual actuation of the inferior aspect of the structure resulting in negative pressure gradients within the internal cavity for fluid expression.

17. The fluid expression device of claim 14, wherein at least one environmental sensor is included within the structure, within the housing, and/or within the receptacle to allow the capturing of environmental data.

18. The fluid expression device of claim 17, further comprising a controller configured to process and quantify the data and make the data available for user and researcher data collection and analysis, as well as to automate pump settings specific to individual users, and optimize fluid expression and minimize discomfort.

19. The fluid expression device of claim 14, wherein the device is configured to automatically transition between a stimulative and non-stimulative cycle multiple times throughout a fluid expression session.

20. The fluid expression device of claim 14, wherein the device is configured to be controlled using a web/mobile user interface accessible from a user's smartphone, tablet or another remotely connectable device.

* * * * *